United States Patent
Van Roon et al.

(10) Patent No.: US 10,981,964 B2
(45) Date of Patent: *Apr. 20, 2021

(54) FUSION PROTEIN COMPRISING IL-4 AND IL-10

(71) Applicant: Synerkine Pharma B.V., Naarden (NL)

(72) Inventors: Joel Adrianus Gijsbert Van Roon, Hilversum (NL); Sarita Aimee Yvonne Hartgring, Utrecht (NL); Cornelis Erik Hack, Utrecht (NL); Christina Louws, Utrecht (NL); Floris Paulus Jacobus Gerardus Lafeber, Houten (NL)

(73) Assignee: Synerkine Pharma B.V., Naarden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/707,435

(22) Filed: Dec. 9, 2019

(65) Prior Publication Data

US 2020/0147178 A1 May 14, 2020

Related U.S. Application Data

(63) Continuation of application No. 15/842,353, filed on Dec. 14, 2017, now Pat. No. 10,851,143, which is a continuation of application No. 14/356,855, filed as application No. PCT/NL2012/050790 on Nov. 8, 2012, now abandoned.

(60) Provisional application No. 61/691,816, filed on Aug. 22, 2012, provisional application No. 61/556,843, filed on Nov. 8, 2011.

(51) Int. Cl.
| | |
|---|---|
| *A61K 38/20* | (2006.01) |
| *C07K 14/54* | (2006.01) |
| *A61K 9/00* | (2006.01) |
| *A61K 9/08* | (2006.01) |
| *A61K 45/06* | (2006.01) |
| *A61K 38/00* | (2006.01) |

(52) U.S. Cl.
CPC ........ *C07K 14/5428* (2013.01); *A61K 9/0029* (2013.01); *A61K 9/0095* (2013.01); *A61K 9/08* (2013.01); *A61K 38/2026* (2013.01); *A61K 38/2066* (2013.01); *A61K 45/06* (2013.01); *C07K 14/5406* (2013.01); *A61K 38/00* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 4,399,216 A | 8/1983 | Axel et al. | |
| 4,634,665 A | 1/1987 | Axel et al. | |
| 5,179,017 A | 1/1993 | Axel et al. | |
| 5,567,611 A | 10/1996 | Ralph et al. | |
| 5,601,815 A | 2/1997 | Powrie et al. | |
| 5,951,973 A | 9/1999 | Lee et al. | |
| 5,986,059 A | 11/1999 | Shanafelt et al. | |
| 6,428,985 B1 | 8/2002 | Bromberg et al. | |
| 7,141,651 B2 | 11/2006 | Gillies et al. | |
| 7,261,882 B2 | 8/2007 | Watkins | |
| 7,749,490 B2 | 7/2010 | Sommer et al. | |
| 8,404,814 B2 | 3/2013 | Neri et al. | |
| 2004/0072299 A1 | 4/2004 | Gillies et al. | |
| 2006/0246032 A1 | 11/2006 | Strom et al. | |
| 2010/0028296 A1 | 2/2010 | Chavez et al. | |
| 2013/0096058 A1 | 4/2013 | Baca et al. | |
| 2013/0316404 A1 | 11/2013 | Roers et al. | |
| 2014/0314712 A1 | 10/2014 | Van Roon et al. | |
| 2018/0094037 A1 | 4/2018 | Van Roon et al. | |

FOREIGN PATENT DOCUMENTS

| | | |
|---|---|---|
| CN | 1382158 A | 11/2002 |
| CN | 104136457 A | 11/2014 |
| CN | 108129574 A | 6/2018 |
| EP | 1731531 A2 | 12/2006 |
| EP | 2776460 B1 | 5/2018 |
| JP | 6284482 B2 | 2/2018 |
| JP | 6527925 B2 | 6/2019 |
| WO | WO-9319770 A1 | 10/1993 |
| WO | WO-95/03411 | 2/1995 |
| WO | WO-9833516 A1 | 8/1998 |
| WO | WO-0110912 A1 | 2/2001 |
| WO | WO-2006079169 A1 | 8/2006 |
| WO | WO-2010040105 A2 | 4/2010 |
| WO | WO-2011108937 A1 | 9/2011 |

(Continued)

OTHER PUBLICATIONS

Backonja MM, Coe CL, Muller DA, & Schell K (2008) Altered cytokine levels in the blood and cerebrospinal fluid of chronic pain patients. J Neuroimmunol 195(1-2):157-163.

Bijlsma, et al., (2002). Suppression of inflammation and joint destruction in rheumatoid arthritis may require a concerted action of Th2 cytokines. Current opinion in investigational drugs (London, England: 2000), 3(7), 1011-1016.

Cavaillon, Jean-Marc, "Pro-versus Anti-Inflammatory Cytokines: Myth or Reality", Cellular and Molecular Biology 47 (4), 000-000, pp. 1-8.

De Jong, et al., "Pan-DR-Binding Hsp60 Self Epitopes Induce and Interleukin-10-Mediated Immune Response in Rheumatoid Arthritis", Arthritis & Rheumatism, vol. 60, No. 7 Jul. 2009, pp. 1966-1976.

(Continued)

*Primary Examiner* — Dong Jiang
(74) *Attorney, Agent, or Firm* — Wilson Sonsini Goodrich & Rosati

(57) ABSTRACT

The invention is concerned with a fusion protein, a nucleic acid molecule encoding such fusion protein, a vector comprising such nucleic acid molecule, and a host cell comprising such nucleic acid molecule or such vector. The invention further pertains to a method for producing such fusion protein. The fusion protein or a gene therapy vector encoding the fusion protein may be used in the prevention or treatment of osteoarthritis, chronic pain, a condition characterized by local or systemic inflammation, immune activation, and/or lymphoproliferation.

26 Claims, 13 Drawing Sheets

Figure 1:
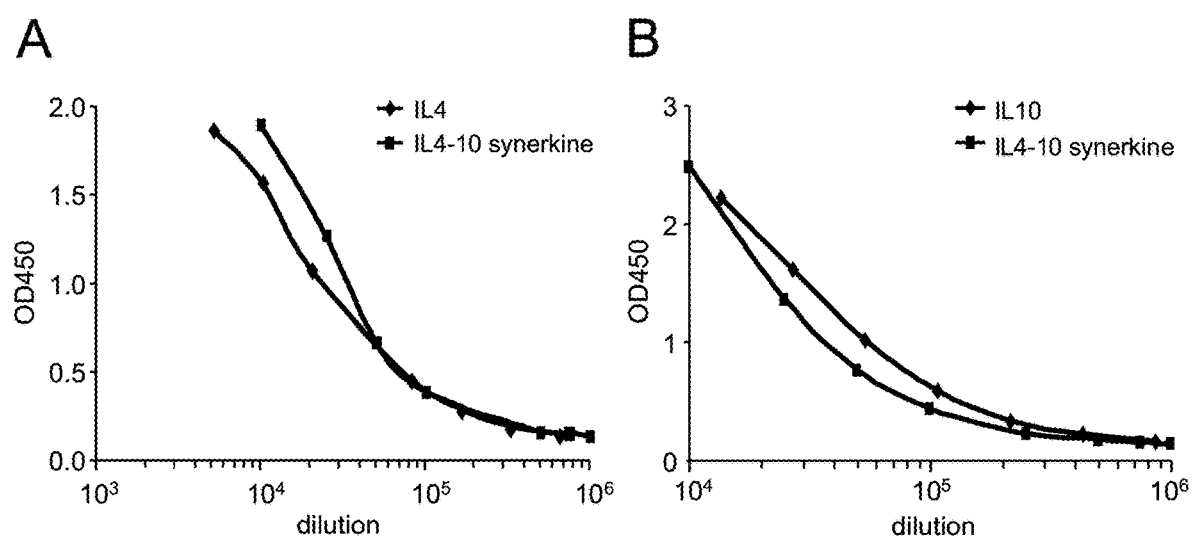

Specification includes a Sequence Listing.

(56) References Cited

FOREIGN PATENT DOCUMENTS

WO    WO-2013070076 A1    5/2013

OTHER PUBLICATIONS

De Oliveira, et al. "Cytokines and Pain" Rev Bras Anestesiol 2011: 61:2, 255-265.
Durocher, et al., "High-level an high-throughput recombinant protein production by transient transfection of suspension-growing human 293-EBNA1 cells", Nucleic Acids Research, 2002, vol. 30, No. 2e9, pp. 1-9.
Guichelaar, et al., "Cartilage proteoglycan-specific T cells as vectors of immunomodulatory biologicals in chronic proteoglycan-induced arthritis", Molecular Immunology 45 (2008) 3526-3535.
Hagenacker T, Czeschik JC, Schafers M, & Busselberg D (2010) Sensitization of voltage activated calcium channel currents for capsaicin in nociceptive neurons by tumor-necrosis-factor-alpha. Brain Res Bull 81(1):157-163.
Hao S, Mata M, Glorioso JC, & Fink DJ (2006) HSV-mediated expression of interleukin-4 in dorsal root ganglion neurons reduces neuropathic pain. Mol Pain 2:6.
Hartgring, S.A.Y., "Role of IL-7 and TSLP in immunopathology of (rheumatoid) arthritis", ISBN: 978-90-393-52-199, University Medical Center Utrecht, pp. 1-185.
Henikoff, et al., "Amino acid substitution matrices from protein blocks", Proc. Natl. Acad. Sci. USA, vol. 89, pp. 10915-10919, Nov. 1992, Biochemistry.
Hwang, et al. "IL-17 induces production of IL-6 and IL-8 in rheumatoid arthritis synovial fibroblasts via VF-kB-and PI3-kinase/Akt-dependent pathways" Arthritis Research & Therapy, vol. 6 No. 2.
International Search Report, PCT/NL2012/050790, dated Mar. 8, 2013.
Jansen, et al., "Protective Abilities of Interleukin-10 in Case of Blood-Induced Joint Damage" University Medical Center Utrecht, Netherlands (2008).
Jansen, et al., "Interleukin-10 Projects Against Blood-Induced Joint Damage", Rheumatology & Clinical Immunology, University Medical Center Utrecht (2007).
Jansen, et al., "Interleukin-10 protects against blood-induced joint damage", British Journal of Hematology, 142, 953-961.
Jansen, et al., "Protective Abilities of Interleukin-10 in Blood-Induced Cartilage Damage", P160, UMC Utrecht, The Netherlands (2006).
Kraus J, et al. (2001) Regulation of mu-opioid receptor gene transcription by interleukin-4 and influence of an allelic variation within a STAT6 transcription factor binding site. J Biol Chem 276(47):43901-43908.
Lauw, et al., "Proinflammatory Effects of IL-10 During Human Endotoxemia", The Journal of Immunology, 2000, 165:2783-2789.
Ledeboer A, et al. (2007) Intrathecal interleukin-10 gene therapy attenuates paclitaxel-induced mechanical allodynia and proinflammatory cytokine expression in dorsal root ganglia in rats. Brain Behav Immun 21(5):686-698.
Lee et al. (2003) Journal of Controlled Release 88(2) p. 333-342. Prevention of autoimmune insulitis by delivery of a chimeric plasmid encoding interleukin-4 and interleukin-10 journal of controlled release.
Milligan ED, Penzkover KR, Soderquist RG, & Mahoney MJ (2012) Spinal interleukin-10 therapy to treat peripheral neuropathic pain. Neuromodulation 15(6):520-526; discussion 526.
Nicola, et al., "General Classes and Functions of Four-Helix Bundle Cytokines", Advanced in Protein Chemistry, vol. 52, p. 1-65.
Pils MC, et al. (2010) Monocytes/macrophages and/or neutrophils are the target of IL-10 in the LPS endotoxemia model. Eur J Immunol 40(2):443-448.
Ren K & Dubner R (2010) Interactions between the immune and nervous systems in pain. Nat Med 16(11):1267-1276.
Soderquist RG, et al. (2010) Release of plasmid DNA-encoding IL-10 from PLGA microparticles facilitates long-term reversal of neuropathic pain following a single intrathecal administration. Pharm Res 27(5):841-854.
Uceyler N, Eberle T, Rolke R, Birklein F, & Sommer C (2007) Differential expression patterns of cytokines in complex regional pain syndrome. Pain 132(1-2):195-205.
Uceyler N, et al. (2006) Reduced levels of antiinflammatory cytokines in patients with chronic widespread pain. Arthritis Rheum 54(8):2656-2664.
Urlaub, et al., "Isolation of Chinese hamster cell mutants deficient in dihydrofolate reductase activity", Pro. Natl. Aca. Sci. USA, vol. 77, No. 7, pp. 4216-4220, Jul. 1960.
Vale, et al., "Antinociceptive Effects of Interleukin-4, -10, and -13 on the Writhing Response in Mice and Zymosan-Induced Knee Joint Incapacitation in Rats", The Journal of Pharmacology and Experimental Therapeutics, vol. 301, No. 1. pp. 102-108.
Van Meegeren, et al., "IL-4 alone and in combination with IL-10 protects against blood-induced cartilage damage", Osteoarthritis and Cartilage 20 (2012) 764-772.
Van Meegeren, et al., "A single intra-articular injection with IL-4 plus IL-10ameliorates blood-induced cartilagedegeneration in haemophilic mice", British Journal of Haematology, 2013, 160, 515-520.
Van Meegeren, et al., "The Combination of IL-4 and IL-10 Protects Against Blood-Induced Cartilage Damage", Osteoarthritis and Cartilage 18, Supplement 2 (2010) S45-S256.
Van Meegeren, Monique Elisabeth Renee, "Blood-induced joint damage: novel targets for therapy", Geboren op Apr. 24, 1983 (2012) pp. 1-180.
Van Roon, et al., (2003). Interleukin 10 treatment of patients with rheumatoid arthritis enhances Fc gamma receptor expression on monocytes and responsiveness to immune complex stimulation. The Journal of rheumatology, 30(4), 648-651.
Van Roon, et al., "Decrease in Peripheral type 1 over type 2 T ell cytokine production in patients with rheumatoid arthritis correlates with an increase in severity of disease", Annals of the Rheumatic Diseases 1997; 56: 656-660.
Van Roon, et al., "Differentiation of naïve CD4+ T cells towards T helper 2 cells is not impaired in rheumatoid arthritis patients", Arthritis Res Ther 2003, 5:R269-R276.
Van Roon, et al. "Proinflammatory cytokine production and cartilage damage due to rheumatoid synovial T helper-1 activation is inhibited by interleukin-4", Annals of the Rheumatic Disease 1995; 54: 836-840.
Van Roon, et al., "Stimulation of Suppressive T Cell Response by Human but not Bacterial 60-kD Heat-shock Protein in Synovial Fluid of Patients with Rheumatoid Arthritis", The American Society for Clinical Investigation, Inc., vol. 100, No. 2, Jul. 1997, 459-463.
Van Roon, et al., "Synergistic Activity of Interleukin-4 and Interleukin-10 in Suppression of Inflammation and Joint Destruction in Rheumatoid Arthritis", Arthritis & Rheumatish, vol. 44, No. 1, Jan. 2001, pp. 3-12.
Verhoef, C. M., et al. (2001). Interleukin 10 (IL-10), not IL-4 or interferon-gamma production, correlates with progression of joint destruction in rheumatoid arthritis. The Journal of rheumatology, 28(9), 1960-1966.
Verhoef, et al., "The immune suppressive effect of dexamethasone in theumatoid arthritis is accompanied by upregulation of interleukin 10 and by differential changes in interferon and interleukin 4 production", Ann Rheum Dis 1999; 58: 49-54.
Wijngaarden, et al., "A Shift in the Balance of Inhibitory and Activating FCγ Receptors on Monocytes Toward the Inhibitory FCγ Receptor lib Is Associated with Prevention of Monocyte Activation in Theumatoid Arthritis", Arthritis & Rheumatism, vol. 50, No. 12, 2004, pp. 3878-3887.
Zdanov, Alexander "Structural analysis of cytokines comprising the IL-10 family", Cytokine & Growth Factor Reviews 21 (2010) 325-330.
Zhang, et al, "Cytokines, Inflammation, and Pain", Department of Anesthesiology and Department of Anesthesiology and Pain Medicine, pp. 26-37.

(56) References Cited

OTHER PUBLICATIONS

Eijkelkamp, et al., "IL4-10 Fusion Protein Is a Novel Drug to Treat Persistent Inflammatory Pain" The Journal of Neuroscience, Jul. 13, 2016; 36(28):7353-7363.

Van Roon, et al., (2002). Suppression of inflammation and joint destruction in rheumatoid arthritis may require a concerted action of Th2 cytokines. Current opinion in investigational drugs (London, England: 2000), 3(7), 1011-1016.

Ding, et al., "A Single Amino Acid Determines the Immunostimulatory Activity of Interleukin 10", (2000) J. Exp. Med. vol. 191, No. 2, pp. 213-223.

Junttila, et al., "Redirecting cell-type specific cytokine responses with engineered interleukin-4 superkines" (2012) Nat Chem Bio. 8(12): 990-998.

Kreitman, et al., "Site-Specific Conjugation to Interleukin 4 Containing Mutated Cysteine Residues Produces Interleukin 4-Toxin Conjugates with Improved Binding an Activity" Biochemistry (1994) 33, 11637-11644.

Kruse, et al., "Site-directed mutagenesis reveals the importance of disulfide bridges and aromatic residues for structure and proliferative activity of human Interleukin-4" Federation of European Biochemical Societies, (1991) vol. 286, No. 1,2 58-60.

Kruse, et al., "Two distinct functional sites of human interleukin 4 are identified by variants impaired in either receptor binding or receptor activation" The EMBO Journal (1993) vol. 12, No. 13, pp. 5121-5129.

Letzelter, et al., "The interleukin-4 site-2 epitope determining binding of the common receptor γ chain" Eur. J. Biochem. (1998) 257, 11-20.

Morrison, et al., "A Receptor Binding Domain of Mouse Interleukin-4 Defined by a Solid-phase Binding Assay in in Vitro Mutagenesis", The Journal of Biological Chemistry, (1992) vol. 267, No. 17, Issue of Jun. 15, pp. 11957-11963.

Van Roon, et al., "Prevention and Reversal of Cartilage Degradation in Rheumatoid Arthritis by Interleukin-10 and Interleukin-4", Arthritis & Rheumatism, vol. 39, No. 5, May 1996, pp. 829-835.

Wang, et al., "A mixed-charge pair in human interleukin 4 dominates high-affinity interaction with the receptor α chain" Proc. Natl. Acad. Sci. USA (1997) vol. 94, pp. 1657-1662.

Westerhof, et al., "3D Domain Swapping Causes Extensive Multimerisation of Human Interleukin-10 When Expressed in Planta", PLOSONE, (2012) vol. 7, Issue 10, pp. 1-10.

Yoon, et al., "Conformational Changes Mediate Interleukin-10 Receptor 2 (IL-10R2) Binding to IL-10 and Assembly of the Signaling Complex" (2006) The Journal of Biological Chemistry, vol. 281, No. 46, pp. 35088-35096.

FUSION PROTEIN COMPRISING IL-4 AND IL-10

CROSS REFERENCE

This application is a continuation of U.S. patent application Ser. No. 15/842,353, filed Dec. 14, 2017, now U.S. Pat. No. 10,851,143, which is a continuation of U.S. patent application Ser. No. 14/356,855 filed May 7, 2014, which is a National Phase Entry of PCT/NL2012/050790 filed on Nov. 8, 2012, which claims priority under 35 U.S.C. 119(e) to U.S. Provisional Application No. 61/556,843 filed on Nov. 8, 2011, and U.S. Provisional Application No. 61/691,816 filed on Aug. 22, 2012, each of which is expressly incorporated herein by reference in its entirety.

FIELD OF THE INVENTION

The present invention is in the field of immunology and pharmacology, particularly for treatment of osteoarthritis, chronic pain, inflammatory diseases or disorders, and related diseases and disorders. The invention particularly relates to a novel fusion protein comprising interleukin 4 (IL4) and interleukin 10 (IL10), optionally physically fused together by a linker. Particularly, the present invention provides an IL4-IL10 fusion protein endowed with a superior biological activity over a combination of the individual cytokines. The present invention also provides nucleic acid sequences encoding a IL4-IL10 fusion protein, expression vectors comprising such nucleic acid sequences, host cells or host organisms altered to harbour the nucleic acid sequence encoding the IL4-IL10 fusion protein and the IL4-IL10 fusion protein itself. The invention further provides methods for producing an IL4-IL10 fusion protein using a cell or organism harbouring such nucleic acid sequences. Transgenic organisms comprising the nucleic acid sequence of the invention are also provided. The present invention also relates to pharmaceutical compositions comprising the IL4-IL10 fusion protein. Finally, the use of the IL4-IL10 fusion protein as a medicament, in particular for the prevention and/or treatment of osteoarthritis and/or conditions characterized by local or systemic inflammation, immune activation, lymphoproliferation and/or chronic pain is taught herein.

BACKGROUND OF THE INVENTION

Inflammatory diseases and their related conditions, such as local or systemic inflammation, immune activation, and/or lymphoproliferation is selected from the group consisting of sepsis, adult respiratory distress syndrome, allo- and xenotransplantation, dermatitis, inflammatory bowel disease, sarcoidosis, allergies, psoriasis, ankylosing spondylarthitis, autoimmune diseases such as systemic lupus erythematosus and rheumatoid arthritis, glomerolonephritis, immune complex-induced and other forms of vasculitis, multiple sclerosis, Sjogren's disease, gout, lymphoproliferatieve diseases such as non Hodgkin lymphoma and B cell chronic lymphocytic leukemia, burn injuries, multiple trauma, stroke, myocardial infarction, atherosclerosis, diabetes mellitus, extracorporeal dialysis and blood oxygenation, ischemia-reperfusion injuries, toxicity induced by the in vivo administration of cytokines or therapeutic monoclonal antibodies, chronic pain syndrome, and neuropathic and/or inflammatory pain, are among the most debilitating conditions observed in clinical practice. The inflammation process is central to these medical conditions, where both pro-inflammatory cytokines and anti-inflammatory cytokines play important roles as mediators of the inflammatory processes.

Pro-inflammatory cytokines promote local and systemic inflammation. Among the large groups of pro-inflammatory cytokines, two are particularly prominent, i.e. the tumour necrosis factor (TNFα) and interleukin 1 (IL1β). A great deal of efforts has been devoted toward developing therapeutic strategies aimed at inhibiting TNFα and IL1β. Specifically, reducing the biological activities of TNFα and IL1β has been accomplished by several strategies such as neutralizing antibodies, soluble receptors, receptor antagonists, and inhibitors of proteases that convert inactive precursors to active molecules. For example, inhibitors of TNFα, such as Infliximab® (anti-TNFα antibody), Humira® (fully human anti-TNFα antibody), Enbrel® (TNF-receptor-Fc-fusion protein), and Anakinra (Kineret®; IL1 receptor antagonist, IL1ra) have been tested in clinical trials. Although blocking TNFα and/or IL1β was successful in many patients suffering from rheumatoid arthritis and inflammatory bowel diseases, not all patients respond well to such type of therapeutic interventions. Therefore, there is still a great need for alternative and effective therapeutic strategies for the treatment of inflammatory diseases, chronic pain, and related conditions.

Osteoarthritis (OA) is the most common joint disorder, and there is evidence that a majority of individuals over the age of 65 have radiographic and/or clinical evidence of OA. The most frequently affected sites are the hands, knees, hips, and spine. Importantly, the symptoms are often associated with significant functional impairment, as well as signs and symptoms of inflammation, including pain, stiffness, and loss of mobility. The characteristic structural changes in OA include the progressive loss of articular cartilage, increased subchondral plate thickness, formation of new bone at the joint margins (osteophytes) and the development of subchondral bone cysts. In addition, at the junction of the articular hyaline cartilage and adjacent subchondral bone, in the region of the so-called tidemark, there is a remnant of calcified cartilage. As OA progresses, there is evidence of vascular invasion and advancement of this zone of calcified cartilage into the articular cartilage that further contributes to a decrease in articular cartilage thickness. These structural alterations in the articular cartilage and peri-articular bone may lead to modifications of the contours of the adjacent articulating surfaces. These changes, as well as the accompanying alterations in subchondral bone remodeling and modulus, may further contribute to the development of an adverse biomechanical environment and enhance the progression of the articular cartilage deterioration. Multiple factors have been shown to affect the progression of OA, including the presence of polyarticular disease, increasing age, associated intra-articular crystal deposition, obesity, joint instability and/or misalignment, muscle weakness, and peripheral neuropathy. These factors can be segregated into categories that include hereditary contributions, mechanical factors, and the effects of ageing. Only very limited therapeutical interventions are proposed for the treatment of OA, and the few therapeutical interventions available are aimed at pain management rather than treatment of the functional impairments.

Therefore, there is a need for providing a single molecule for which clinical development is feasible and that may be used for prevention or treatment of OA, as well as chronic pain, and for prevention or treatment of a condition characterized by a local or systemic inflammation, immune activation, and/or lymphoproliferation. This would enable clinical development of a single molecule for multiple diseases or disorders with very different etiology.

SUMMARY OF THE INVENTION

In a first aspect, the present invention relates to a fusion protein comprising an interleukin 4 (IL4) and interleukin 10 (IL10).

In an embodiment, said IL4 and said IL10 are linked by a linker.

In an embodiment, the IL4 is fused N-terminal of the IL10.

In an embodiment, the IL10 is fused N-terminal of the IL4.

In an embodiment, said fusion protein further comprises one or more chemical modifications. Said chemical modifications may be selected from the group consisting of glycosylation, fucosylation, sialylation, and pegylation.

In an embodiment, said IL10 is human IL10.

In an embodiment said IL4 is human IL4.

In a second aspect, the present invention pertains to a nucleic acid molecule comprising a polynucleotide encoding the fusion protein taught herein.

In another aspect, the present invention is directed to a vector comprising the nucleic acid molecule taught herein.

In an aspect, the present invention is concerned with a host cell comprising the nucleic acid molecule taught herein or the vector taught herein.

In an aspect, the present invention provides a method for producing a fusion protein as taught herein, said method comprising the steps of: culturing a host cell as taught herein under conditions permitting the production of the fusion protein as taught herein; and optionally, recovering the fusion protein.

In yet in another aspect, the present invention provides for a pharmaceutical composition comprising the fusion protein as taught herein, and a pharmaceutically acceptable carrier.

The invention also pertains to a fusion protein as taught herein for use as a medicament, such as for use in the prevention or treatment of a condition characterized by local or systemic inflammation, immune activation, lymphoproliferation and/or pain.

Said condition characterized by local or systemic inflammation, immune activation, lymphoproliferation and/or chronic pain may be selected from the group consisting of: sepsis, adult respiratory distress syndrome, allo- and xeno-transplantation, dermatitis, inflammatory bowel disease, sarcoidosis, allergies, psoriasis, osteoarthritis, ankylosing spondylarthitis, autoimmune diseases such as systemic lupus erythematosus and rheumatoid arthritis, glomerolonephritis, immune complex-induced and other forms of vasculitis, multiple sclerosis, Sjogren's disease, gout, lymphoproliferatieve diseases such as non Hodgkin lymphoma and B cell chronic lymphocytic leukemia, burn injuries, multiple trauma, stroke, myocardial infarction, atherosclerosis, diabetes mellitus, extracorporeal dialysis and blood oxygenation, ischemia-reperfusion injuries, peripheral neuropathy, toxicity induced by the in vivo administration of cytokines or therapeutic monoclonal antibodies, chronic pain syndrome, and neuropathic and/or inflammatory pain.

In an aspect, the invention relates to a fusion protein as taught herein for use in the prevention or treatment of a clinical condition in a mammal, such as a human, for which IL10 is indicated.

The invention is also concerned with a fusion protein as taught herein for use in the prevention or treatment of a clinical condition in a mammal, such as a human, for which IL4 is indicated.

Finally, the invention teaches a vector as taught herein for use in the prevention or treatment of a condition characterized by local or systemic inflammation, immune activation, lymphoproliferation and/or chronic pain, which condition may be selected from the group consisting of: sepsis, adult respiratory distress syndrome, allo- and xenotransplantation, dermatitis, inflammatory bowel disease, sarcoidosis, allergies, psoriasis, osteoarthritis, ankylosing spondylarthitis, autoimmune diseases such as systemic lupus erythematosus and rheumatoid arthritis, glomerolonephritis, immune complex-induced and other forms of vasculitis, multiple sclerosis, Sjogren's disease, gout, lymphoproliferatieve diseases such as non Hodgkin lymphoma and B cell chronic lymphocytic leukemia, burn injuries, multiple trauma, stroke, myocardial infarction, atherosclerosis, diabetes mellitus, extracorporeal dialysis and blood oxygenation, ischemia-reperfusion injuries, toxicity induced by the in vivo administration of cytokines or therapeutic monoclonal antibodies, chronic pain syndrome, and neuropathic and/or inflammatory pain.

DETAILED DESCRIPTION OF THE INVENTION

General Definitions

The term "nucleic acid molecule" (or "nucleic acid sequence", "polynucleotide", or "nucleotide sequence") refers to a DNA or RNA molecule in single or double stranded form, particularly a DNA encoding a protein according to the invention. An "isolated nucleic acid sequence" refers to a nucleic acid sequence which is no longer in the natural environment from which it was isolated, e.g., the nucleic acid sequence in a bacterial host cell or in the plant nuclear or plastid genome.

The terms "protein" or "polypeptide" are used interchangeably and refer to molecules consisting of a chain of amino acids, without reference to a specific mode of action, size, 3 dimensional structure or origin. An "isolated protein" is used to refer to a protein which is no longer in its natural environment, for example in vitro or in a recombinant bacterial or plant host cell.

The term "fusion protein" refers to a protein or polypeptide that has an amino acid sequence derived from two or more proteins. The fusion protein may also include linking regions or a linker of amino acids between amino acid portions derived from separate proteins.

The term "IL4-IL10 fusion protein" refers to a fusion polypeptide comprising at least IL4 and IL10, optionally coupled to one another via a linker. The fusion protein may comprise additional polypeptide sequences, e.g., a signal sequence, a Histidine-tag, an antibody Fc fragment, and the like.

As used herein, a "linker" means a polypeptide used to couple two proteins or polypeptides, in casu IL4 and IL10. The linker typically is a stretch of amino acids, e.g., predominantly glycine and/or serine. In an embodiment, the linker is a stretch of amino acids having a length of up to 100 nucleotides, such as from about 2, 5, 7, 10, 15 amino acids up to about 15, 20, 25, 30, 35, 50, 75, or 100 amino acids, preferably comprising predominantly serine and glycine residues.

As used herein, "interleukin 10" (IL10) refers to any mammalian IL10, such as human IL10, mouse IL10, or an active species or allelic variant, fragment or derivative thereof.

As used herein, "interleukin 4" (IL4) refers to any mammalian IL4, such as human IL4, mouse IL4, or an active species or allelic variant, fragment or derivative thereof.

As used herein, the term "dimeric" refers to a molecule wherein two polypeptides are associated stably through covalent or non-covalent interactions. The term "homodimeric" refers to a molecule wherein two identical polypeptides are associated stably through covalent or non-covalent interactions. In a suitable embodiment, they are associated stably through non-covalent interactions.

"Functional", in relation to the fusion proteins of the present invention (or variants or fragments thereof), refers to the capability to display both IL4 and IL10 functionality. A functional assay for IL4 and IL10 is the lipopolysaccharide (LPS)-induced cytokine release (e.g. IL1, IL6, IL8, TNFα) in whole blood.

The term "gene" means a DNA sequence comprising a region (transcribed region), which is transcribed into a RNA molecule (e.g. a mRNA) in a cell, operably linked to suitable regulatory regions (e.g. a promoter). A gene may thus comprise several operably linked sequences, such as a promoter, a 5' leader sequence comprising e.g. sequences involved in translation initiation, a (protein) coding region (cDNA or genomic DNA), introns, and a 3'non-translated sequence comprising e.g. transcription termination sites.

A "3' UTR" or "3' non-translated sequence" (also often referred to as 3' untranslated region, or 3'end) refers to the nucleic acid sequence found downstream of the coding sequence of a gene, which comprises for example a transcription termination site and (in most, but not all eukaryotic mRNAs) a polyadenylation signal (such as e.g. AAUAAA or variants thereof). After termination of transcription, the mRNA transcript may be cleaved downstream of the polyadenylation signal and a poly(A) tail may be added, which is involved in the transport of the mRNA to the cytoplasm (where translation takes place).

"Expression of a gene" refers to the process wherein a DNA region, which is operably linked to appropriate regulatory regions, particularly a promoter, is transcribed into an RNA, which is biologically active, i.e. which is capable of being translated into a biologically active protein or peptide (or active peptide fragment). "Expression of a polypeptide" additionally refers to a process wherein an mRNA is translated into a protein product, which may or may not be secreted.

A "transcription regulatory sequence" is herein defined as a nucleic acid sequence that is capable of regulating the rate of transcription of a (coding) sequence operably linked to the transcription regulatory sequence. A transcription regulatory sequence as herein defined will thus comprise all of the sequence elements necessary for initiation of transcription (promoter elements), for maintaining and for regulating transcription, including e.g. attenuators or enhancers. Although mostly the upstream (5') transcription regulatory sequences of a coding sequence are referred to, regulatory sequences found downstream (3') of a coding sequence are also encompassed by this definition.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of ordinary skill in the art to act directly or indirectly to regulate the amount of transcription from the promoter. A "constitutive" promoter is a promoter that is active in most tissues under most physiological and developmental conditions. An "inducible" promoter is a promoter that is physiologically (e.g. by external application of certain compounds) or developmentally regulated. A "tissue specific" promoter is only active in specific types of tissues or cells.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the DNA sequences being linked are typically contiguous.

A "nucleic acid construct" or "vector" is herein understood to mean a man-made nucleic acid molecule resulting from the use of recombinant DNA technology and which is used to deliver exogenous DNA into a host cell. Vectors usually comprise further genetic elements to facilitate their use in molecular cloning, such as e.g. selectable markers, multiple cloning sites and the like (see below).

"Stringent hybridisation conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point ($T_m$) for the specific sequences at a defined ionic strength and pH. The $T_m$ is the temperature (under defined ionic strength and pH) at which 50% of the target sequence hybridises to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridisations (Northern blots using a probe of e.g. 100 nt) are for example those which include at least one wash in 0.2×SSC at 63° C. for 20 min, or equivalent conditions. Stringent conditions for DNA-DNA hybridisation (Southern blots using a probe of e.g. 100 nt) are for example those which include at least one wash (usually 2) in 0.2×SSC at a temperature of at least 50° C., usually about 55° C., for 20 min, or equivalent conditions. See also Sambrook et al. (1989) and Sambrook and Russell (2001).

"Sequence identity" and "sequence similarity" can be determined by alignment of two peptides or two nucleotide sequences using global or local alignment algorithms. Sequences may then be referred to as "substantially identical" or "essentially similar" when they (when optimally aligned by for example the programs GAP or BESTFIT using default parameters) share at least a certain minimal percentage of sequence identity (as defined below). GAP uses the Needleman and Wunsch global alignment algorithm to align two sequences over their entire length, maximizing the number of matches and minimises the number of gaps. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff &

Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA, or EmbossWin version 2.10.0 (using the program "needle"). Alternatively percent similarity or identity may be determined by searching against databases, using algorithms such as FASTA, BLAST, etc. Preferably, the sequence identity refers to the sequence identity over the entire length of the sequence.

A "host cell" or a "recombinant host cell" or "transformed cell" are terms referring to a new individual cell (or organism) arising as a result of at least one nucleic acid molecule, especially comprising a nucleic acid molecule encoding a desired protein. The host cell is preferably a plant cell or a bacterial cell. The host cell may contain the nucleic acid molecule or vector of the present invention as an extra-chromosomally (episomal) replicating molecule, or more preferably, comprises the nucleic acid molecule or vector of the present invention integrated in the genome of the host cell.

The term "selectable marker" is a term familiar to one of ordinary skill in the art and is used herein to describe any genetic entity which, when expressed, can be used to select for a cell or cells containing the selectable marker. Selectable marker gene products confer for example antibiotic resistance or nutritional requirements.

The term "biological half-life" refers to the time required for the amount of a substance, e.g., protein, in a biological system, e.g., the circulation within the animal or human body, to be reduced to one half of its value by biological processes such as renal clearance and degradation.

In this document and in its claims, the verb "to comprise" and its conjugations is used in its non-limiting sense to mean that items following the word are included, but items not specifically mentioned are not excluded. It also encompasses the more limiting verb "to consist of". In addition, reference to an element by the indefinite article "a" or "an" does not exclude the possibility that more than one of the element is present, unless the context clearly requires that there be one and only one of the elements. The indefinite article "a" or "an" thus usually means "at least one". It is further understood that, when referring to "sequences" herein, generally the actual physical molecules with a certain sequence of subunits (e.g. amino acids) are referred to.

Proteins, Nucleic Acid Sequences, Vectors and Host Cells of the Invention

The present inventors have now devised a novel "single molecule therapy". Specifically, the inventors provide a fusion protein comprising an IL4 protein and an IL10 protein, optionally physically fused together via a linker. Particularly, the fusion protein of the present invention was found to have a superior biological activity (e.g. inhibits TNFα and IL1β) over its individual counterparts, i.e., IL4 and IL10 separately. Specifically, it was found that the fusion protein of the present invention was significantly larger (~35 kD) than the individual cytokines (both<20 kD). The present inventors also unexpectedly found that the fusion protein itself forms dimers (via the IL10 portion of the fusion protein), thus providing a fusion protein with an even larger molecular weight (~70 kD). Such increase in molecular weight, and consequently the molecular radius, not only significantly prolongs the biological half-life of the IL4-IL10 fusion protein in the circulation compared to the individual cytokines, but also increases its bioavailability at the site of inflammation to an unprecedented level. The fusion protein of the present invention also greatly lengthens the therapeutic time window for synergetic effects between IL4 and IL10 to occur, since the fusion protein delivers both cytokines at the site of inflammation, where they can both exert their actions for an equal amount of time in each other's presence. Furthermore, it was found unexpectedly that the fusion protein of the present invention also exerts a dual therapeutic action. Specifically, the IL4-IL10 fusion protein was shown to act as an anti-inflammatory agent when administered systematically while it acted as an anti-hyperalgesia agent when administered intrathecally.

In one embodiment of the invention nucleic acid sequences and amino acid sequences of the IL4-IL10 fusion proteins are provided (including variants and fragments thereof). The IL4-IL10 fusion proteins, as well as functional fragments and variants thereof, display IL4 activity as well as IL10 activity.

In one aspect, a fusion protein comprising IL4 and IL10 is provided. The fusion protein comprises an IL4 protein, or a variant or fragment thereof. The IL4 protein is preferably a mammalian IL4 protein, such as a human IL4, or mouse IL4. One amino acid sequence of IL4 is set forth in SEQ ID NO:1. Variants of IL4 include, for example, proteins having at least 70%, 75%, 80%, 85%, 90%, 92%, 95%, 96%, 97%, 98%, 99% or more, such as 100%, amino acid sequence identity to SEQ ID NO:1, preferably over the entire length. Amino acid sequence identity is preferably determined by pairwise alignment using the Needleman and Wunsch algorithm and GAP default parameters as defined above. Variants also include proteins having IL4 activity, which have been derived, by way of one or more amino acid substitutions, deletions or insertions, from the polypeptide having the amino acid sequence of SEQ ID NO:1. Preferably, such proteins comprise from 1, 2, 3, 4, 5, 6, 7, 8, 9, 10 or more up to about 100, 90, 80, 70, 60, 50, 45, 40, 35, 30, 25, 20, 15 amino acid substitutions, deletions or insertions.

The fusion protein further comprises an IL10 protein, or a variant or fragment thereof. The IL10 protein is preferably a mammalian IL10 protein, such as a human IL10, or mouse IL10. One amino acid sequence representing IL10 is set forth in SEQ ID NO:2. Variants of IL10 include, for example, proteins having at least 70%, 75%, 80%, 85%, 90%, 92%, 95%, 96%, 97%, 98%, 99% or more, such as 100%, amino acid sequence identity to SEQ ID NO:2, preferably over the entire length. Amino acid sequence identity is preferably determined by pairwise alignment using the Needleman and Wunsch algorithm and GAP default parameters as defined above. Variants also include proteins having IL10 activity, which have been derived, by way of one or more amino acid substitutions, deletions or insertions, from the polypeptide having the amino acid sequence of SEQ ID NO:2. Preferably, such proteins comprise from 1, 2, 3, 4, 5, 6, 7, 8, 9, 10 or more up to about 100, 90, 80, 70, 60, 50, 45, 40, 35, 30, 25, 20, 15 amino acid substitutions, deletions or insertions.

The IL4 and IL10 in the fusion protein may or may not be connected by a linker. Additional amino acid sequences may be present at the N- and/or C-terminus of the fusion protein of the present invention, e.g., to facilitate purification. For example, a histidine-tag may be present at the C- or N-terminus to facilitate purification. Alternatively, the IL4-IL10 fusion protein of the invention may optionally comprise additional protein moieties, such as moieties capable of targeting, e.g., a protein moiety comprising one or more antibody Fc regions.

The IL4 may be located N-terminal of the IL10, or may be located C-terminal of the IL10. In a preferred embodiment, the IL4 molecule is located N-terminal of the IL10 molecule. It was found that the latter fusion protein displayed higher specific activity compared to an IL4-IL10 fusion protein in which the IL4 molecule was located C-terminal of the IL10 molecule (data not shown).

The IL4-IL10 fusion protein may be present in its monomeric form, in which case it has a kDa of about 35 kDa, or it may be a dimeric IL4-IL10 fusion protein, i.e., two IL4-IL10 fusion proteins may be associated with one another non-covalently, in which case it has a kDa of about 70 kDa.

In an embodiment, the fusion protein of the invention consists essentially of IL4 and IL10, optionally linked by a linker.

In an embodiment, both the IL4 and the IL10 moieties within the fusion protein of the present invention are active and able to signal cells to downregulate the production of at least one inflammatory cytokine or mediator such as IL1β, IL6, IL8, TNFα. Preferably, at least TNFα, IL6, and IL8 are downregulated.

In an embodiment, the fusion protein inhibits the generation of cytokines such as TNFα, IL1β, IL6, IL8 and other inflammatory cytokines while they induce secretion of inhibitory molecules such as IL1 receptor antagonist and soluble TNF receptors by inflammatory and other cells stimulated by endotoxin, other Toll-like receptor (TLR) agonists, or other stimuli.

In an embodiment, the fusion protein of the present invention inhibits the expression of adhesion molecules by inflammatory, endothelial and other cells stimulated by agonists including endotoxin, other TLR agonists, and others.

In an embodiment, the fusion protein inhibits the expression of tissue factor by endothelial, inflammatory and other cells stimulated by endotoxin, other TLR agonists, or other stimuli.

In an embodiment, the fusion protein of the present invention inhibits the generation of oxygen radicals by inflammatory and other cells stimulated by endotoxin, other TLR agonists, or other stimuli.

In an embodiment, the fusion protein inhibits activity of IFNγ- and IL17 secreting Th1 and Th17 cells and induce or sustain FoxP3-expressing suppressive T cells (CD25+), TGFβ-secreting Th2, Tr1 and Th3 cells generated in vitro in the presence or absence of antigen-presenting cells stimulated by self or non-self antigens, superantigens including *Staphylococcus* enterotoxin B (SEB) or mitogens such including CD3, CD28, phytohemagglutinin (PHA) or phorbol myristate acetate (PMA).

In an embodiment, the fusion proteins inhibit the expression of activating Fcγ receptors while they induce the expression of inhibitory Fcγ receptors preventing activation of cells such as monocytes, macrophages, and dendritic cells by IgG-containing immune complexes.

In a suitable embodiment, the fusion protein of the present invention is present in a homodimeric form.

In one embodiment, it has a molecular weight of above 60 kDa.

The fusion protein of the present invention may be prepared by techniques which are routine to the skilled person. For example, it may be prepared using a technique which provides for the production of recombinant fusion proteins by continuous cell lines in culture. For example, fusion proteins of the present invention can be produced in a host cell transfectoma using a combination of recombinant DNA techniques and gene transfection methods.

For example, to express the fusion proteins of the present invention, a nucleic acid molecule encoding the fusion proteins of the present invention can be prepared by standard molecular biology techniques. The nucleic acid molecule of the invention is preferably operably linked to transcription regulatory sequences such as a promoter, and optionally a 3' untranslated region. The nucleic acid molecule of the present invention may be inserted into a vector, such as an expression vector, such that the genes are operatively linked to transcriptional and translational control sequences. The expression vector and transcription regulatory sequences are selected to be compatible with the expression host cell used. The nucleic acid molecule encoding a fusion protein of the present invention may be inserted into the expression vector by routine methods. The nucleic acid molecule or vector of the present invention may further include a nucleotide sequence encoding a signal peptide, which may facilitate secretion of the fusion protein from the host cell. Said nucleotide sequence encoding a signal peptide may be operably linked to the nucleic acid molecule of the present invention. Preferably, said signal peptide is located at the amino terminus of the fusion protein of the present invention, and as such, the nucleotide sequence encoding said signal peptide may be located 5' of the nucleic acid molecule encoding the fusion protein of the present invention. The signal peptide may be a cytokine signal peptide or a signal peptide from a non-cytokine protein. The promoter may be constitutive or inducible. The vector may comprise a selectable marker for selection of a vector-carrying host cell. The vector may comprise an origin of replication when the vector is a replicable vector.

The fusion protein according to the invention may be synthesized de novo by chemical synthesis (using e.g. a peptide synthesizer such as supplied by Applied Biosystems) or may be produced by recombinant host cells by expressing the nucleic acid sequence encoding the fusion protein, fragment or variant. Variants and fragments are preferably functional, i.e., have IL4 and/or IL10 activity, preferably IL4 and IL10 activity.

The anti-inflammatory activity and thus functionality of IL4 and IL10, as well as the IL4-IL10 fusion protein can be determined using routine methods. For example, a suitable assay for functionality of IL4 and IL10, as well as the IL4-IL10 fusion protein, is the lipopolysaccharide (LPS) induced cytokine release (IL1β, IL6, IL8, TNFα) in whole blood, e.g., as set forth in Example 6.

In another aspect, isolated nucleic acid sequences encoding any of the above fusion proteins are provided, such as cDNA, genomic DNA, and RNA sequences. Due to the degeneracy of the genetic code various nucleic acid sequences may encode the same amino acid sequence. Any nucleic acid sequence encoding the fusion proteins of the invention are herein referred to as "IL4-IL10 fusion protein encoding nucleic acid sequences". The nucleic acid sequences provided include recombinant, artificial or synthetic nucleic acid sequences. It is understood that when sequences are depicted as DNA sequences while RNA is referred to, the actual base sequence of the RNA molecule is identical with the difference that thymine (T) is replaced by uracil (U). The nucleic acid sequences of the invention are particularly useful for expression of the IL4-IL10 fusion protein of the invention, for either the production of these proteins or for gene therapy purposes.

The nucleic acid sequence, particularly DNA sequence, encoding the IL4-IL10 fusion protein of the invention can be inserted in expression vectors to produce (high amounts of) IL4-IL10 fusion protein. Suitable vectors include, without limitation, linear nucleic acids, plasmids, phagemids, cosmids, RNA vectors, viral vectors and the like. Non-limiting examples of a viral vector include a retrovirus, an adenovirus, and an adeno-associated virus. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP)) and polyoma. Alternatively, nonviral regulatory sequences may be used, such as the ubiquitin promoter.

In addition to the nucleic acid molecules encoding IL4-IL10 fusion proteins and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, all by Axel et al.). For example, typically the selectable marker gene confers resistance to drugs, such as G418, hygromycin or methotrexate, in a host cell into which the vector has been introduced. Preferred selectable marker genes include the dihydrofolate reductase (DHFR) gene (for use in dhfr-host cells with methotrexate selection/amplification) and the neo gene (for G418 selection). Finally, the recombinant expression vector may contain a gene that codes for a glycosyl transferase in addition to the nucleic acid sequence encoding the fusion proteins of the present invention.

In another aspect, the present invention relates to a host cell comprising a nucleic acid sequence of the present invention, or a nucleic acid construct or vector comprising a nucleic acid sequence of the present invention. The host cell may be any host cell. The host cell may be selected from prokaryotic and eukaryotic cells. The host cell may also be a cell line, such as a prokaryotic or eukaryotic cell line. The host cell is preferably an animal cell or cell line, such as a mammalian cell or cell line.

In one embodiment the fusion proteins of the present invention are expressed in eukaryotic cells, such as mammalian host cells. Preferred mammalian host cells for expressing the recombinant IL4-IL10 fusion protein of the invention include CHO cells (including dhfr-CHO cells, described in (Urlaub et al., 1980), used with a DHFR selectable marker, NS/0 myeloma cells, COS cells, HEK293 cells and SP2.0 cells. When recombinant expression vectors comprising nucleic acid sequences encoding IL4-IL10 fusion proteins are introduced into mammalian host cells, the fusion proteins of the present invention may be produced by culturing the host cells for a period of time sufficient to allow for expression of the fusion proteins in the host cells or, more preferably, secretion of the fusion proteins into the culture medium in which the host cells are grown. The fusion proteins of the present invention may be recovered from the culture medium in which the host cells are grown and/or may be purified from the culture medium using standard protein purification methods.

Alternatively the nucleic acid sequences encoding the fusion proteins of the invention can be expressed in other expression systems, including prokaryotic cells, such as microorganisms, e.g. E. coli, algae, as well as insect cells. Furthermore, the fusion proteins of the present invention can be produced in transgenic non-human animals, such as in milk from sheep and rabbits or eggs from hens, or in transgenic plants.

Introduction of the nucleic acid sequence of the present invention into a host cell may be carried out by any standard technique known in the art. For expression of the fusion proteins of the present invention, the expression vector(s) encoding the fusion protein may be transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection, lipofectamine transfection, and freeze-dry method transfection, and the like. Cell lines that secrete the fusion proteins of the present invention can be identified by assaying culture supernatants for the presence of the fusion protein. The preferred screening procedure comprises two sequential steps, the first being identification of cell lines that secrete the fusion protein, the second being determination of the quality of the fusion protein such as the ability of the fusion protein to inhibit cytokine production by blood cells stimulated with LPS or other Toll-like receptor agonists, glycosylation patterns, and others.

For optimal expression in a host cell the IL4-IL10 fusion protein encoding DNA sequences can be codon-optimized by adapting the codon usage to that most preferred in host cell genes. Several techniques for modifying the codon usage to that preferred by the host cells can be found in patent and scientific literature. The exact method of codon usage modification is not critical for this invention.

In another embodiment of the invention, PCR primers and/or probes and kits for detecting the IL4-IL10 fusion protein encoding DNA or RNA sequences are provided. Degenerate or specific PCR primer pairs to amplify IL4-IL10 fusion protein encoding DNA from samples can be synthesized (see Dieffenbach and Dveksler (1995) PCR Primer: A Laboratory Manual, Cold Spring Harbor Laboratory Press, and McPherson at al. (2000) PCR-Basics: From Background to Bench, First Edition, Springer Verlag, Germany). For example, any stretch of 9, 10, 11, 12, 13, 14, 15, 16, 18 or more contiguous nucleotides of an IL4-IL10 fusion protein encoding nucleic acid sequence (or the complement strand) may be used as primer or probe. Likewise, DNA fragments of an IL4-IL10 fusion protein encoding nucleic acid sequence can be used as hybridization probes. A detection kit for an IL4-IL10 fusion protein encoding nucleic acid sequence may comprise primers specific for an IL4-IL10 fusion protein encoding nucleic acid sequence and/or probes specific for an IL4-IL10 fusion protein encoding nucleic acid sequences, and an associated protocol to use the primers or probes to detect specifically IL4-IL10 fusion protein encoding nucleic acid sequence in a sample. Such a detection kit may, for example, be used to determine, whether a host cell has been transformed with a specific IL4-IL10 fusion protein encoding nucleic acid sequence of the invention. Because of the degeneracy of the genetic code, some amino acid codons can be replaced by others without changing the amino acid sequence of the protein.

In an aspect, the present invention is concerned with a method for producing an IL4-IL10 fusion protein, said method comprising the steps of: culturing a host cell of the present invention under conditions permitting the production of the IL4-IL10 fusion protein; and optionally, recovering the fusion protein. The skilled person will be capable of routinely selecting conditions permitting production of the IL4-IL10 fusion proteins of the present invention. Additionally, a person skilled in the art will be capable of recovering the fusion protein produced using routine methods, which include, without limitation, chromatographic methods (including, without limitation, size exclusion chromatography, hydrophobic interaction chromatography, ion exchange chromatography, affinity chromatography, immunoaffinity chromatography, metal binding, and the like), immunoprecipitation, HPLC, ultracentrifugation, precipitation and differential solubilisation, and extraction. As said above, recovery or purification of the fusion proteins of the present invention may be facilitated by adding, for example, a Histidine-tag to the fusion protein.

Pharmaceutical Composition

In an aspect, the invention relates to a pharmaceutical composition comprising the fusion protein of the present invention and a pharmaceutically acceptable carrier.

The pharmaceutical compositions may be formulated with pharmaceutically acceptable carriers or diluents as well as any other known adjuvants and excipients in accordance with conventional techniques (e.g., as described in Remington: The Science and Practice of Pharmacy, $19^{th}$ Edition, Gennaro, Ed., Mack Publishing Co., Easton, Pa., 1995).

The term "pharmaceutically acceptable carrier" relates to carriers or excipients, which are inherently nontoxic and nontherapeutic. Examples of such excipients are, but are not limited to, saline, Ringer's solution, dextrose, solution and Hank's solution. Non-aqueous excipients such as fixed oils and ethyl oleate may also be used. A preferred excipient is 5% dextrose in saline. The excipient may contain minor amounts of additives such as substances that enhance isotonicity and chemical stability, including buffers and preservatives.

The pharmaceutical composition may be administered by any suitable routes and mode. As will be appreciated by the skilled artisan, the route and/or mode of administration will vary depending upon the desired results.

The pharmaceutical compositions according to the invention may be formulated in accordance with routine procedures for administration by any routes, such as oral, topical, parenteral, sublingual, transdermal, or by inhalation. The compositions may be in the form of tablets, capsules, powders, granules, lozenges, creams or liquid preparations, such as oral or sterile parenteral solutions or suspensions or in the form of a spray, aerosol or other conventional method for inhalation.

The pharmaceutical compositions of the present invention include those suitable for oral, nasal, topical (including buccal and sublingual), rectal, vaginal and/or parenteral administration.

In an embodiment, the pharmaceutical composition is administered parenterally.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

In an embodiment the pharmaceutical composition is administered by intra-venous or subcutaneous injection or infusion.

In an embodiment the fusion proteins of the invention are administered in crystalline form by subcutaneous injection.

As used herein, "pharmaceutically acceptable carrier" includes any and all solvents, dispersion media, coatings, antibacterial and antifungal agents, isotonicity agents, antioxidants and absorption delaying agents, and the like that are physiologically compatible.

Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical composition of the invention is contemplated. Preferably, the carrier is suitable for parenteral administration, e.g. intravenous or subcutaneous injection or infusion.

Pharmaceutical compositions typically must be sterile and stable under the conditions of manufacture and storage. The composition can be formulated as a solution, microemulsion, liposome, or other ordered structure suitable to high drug concentration. Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Depending on the route of administration, the active compound, i.e., the IL4-IL10 fusion proteins, may be coated in a material to protect it from the action of acids and other natural conditions that may inactivate the compound. For example, the compound may be administered to a subject in an appropriate carrier, for example, liposomes. Liposomes include water-in-oil-in-water CGF emulsions as well as conventional liposomes (Strejan et al., 1984).

The fusion proteins of the present invention may also be prepared with carriers that will protect it against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Methods for the preparation of such formulations are generally known to those skilled in the art. See, e.g., Sustained and Controlled Release Drug Delivery Systems, J. R. Robinson, ed., Marcel Dekker, Inc., New York, 1978.

Dosage regimens may be adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Actual dosage levels of the IL4-IL10 fusion proteins in the pharmaceutical compositions of the present invention may be varied so as to obtain an amount of the IL4-IL10 fusion protein which is effective ("effective amount") to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion, the duration of the treatment, other drugs, compounds and/or materials used in combination with the particular compositions employed, the age, sex, weight, condition, general health and prior medical history of the patient being treated, and like factors well known in the medical arts.

In one embodiment, the IL4-IL10 fusion proteins of the present invention can be given as intravenous injection or a short infusion, in another embodiment, they are administered by slow continuous infusion over a long period, such as more than 24 hours, in order to reduce toxic side effects.

In yet another embodiment, the IL4-IL10 fusion proteins of the present invention can be administered as maintenance therapy, such as, e.g., once a week for a period of 6 months or more.

Therapeutic Uses

In a further aspect, the present invention relates to the fusion protein of the present invention or a pharmaceutical composition comprising the fusion protein for use as a medicament.

In an aspect, the present invention pertains to the fusion protein of the present invention or a pharmaceutical composition comprising the fusion protein for use in preventing or treating osteoarthritis. Particularly, it was found that the fusion protein of the present invention has a cartilage-protective activity. Therefore, the fusion protein may be used for prevention and treatment of cartilage breakdown, particularly in OA. Additionally, it was found in a canine OA model that dogs given the fusion protein of the present invention experienced significantly less pain as compared to dogs not given the fusion protein of the present invention. As such, the fusion protein of the invention may be particularly useful for prevention or treatment of OA (prevention or treatment of cartilage degradation) with its associated chronic pain.

In a further aspect, the present invention pertains to a fusion protein of the present invention or a pharmaceutical composition comprising the fusion protein for use in prevention or treatment of OA, chronic pain, a condition characterized by local or systemic inflammation, immune activation, and/or lymphoproliferation.

In an embodiment, said condition characterized by local or systemic inflammation, immune activation, and/or lymphoproliferation is selected from the group consisting of: sepsis, adult respiratory distress syndrome, allo- and xeno-transplantation, dermatitis, inflammatory bowel disease, sarcoidosis, allergies, psoriasis, ankylosing spondylarthitis, autoimmune diseases such as systemic lupus erythematosus and rheumatoid arthritis, glomerolonephritis, immune complex-induced and other forms of vasculitis, multiple sclerosis, Sjogren's disease, gout, lymphoproliferatieve diseases such as non Hodgkin lymphoma and B cell chronic lymphocytic leukemia, burn injuries, multiple trauma, stroke, myocardial infarction, atherosclerosis, diabetes mellitus, extracorporeal dialysis and blood oxygenation, ischemia-reperfusion injuries, toxicity induced by the in vivo administration of cytokines or therapeutic monoclonal antibodies, chronic pain syndrome, and neuropathic and/or inflammatory pain.

In an embodiment, said condition is characterized by pain and may be selected from inflammatory pain and neuropathic pain.

In another aspect, the invention is directed to a fusion protein of the present invention for use in the prevention or treatment of a clinical condition in a mammal, such as a human, for which IL10 is indicated.

In a further aspect, the invention is directed to a fusion protein of the present invention for use in the prevention or treatment of a clinical condition in a mammal, such as a human, for which IL4 is indicated.

In an embodiment of the invention the fusion polypeptide of the invention is used for preventing or treating a disease or disorder, wherein inhibition of the production of pro-inflammatory cytokines and other inflammatory mediators is beneficial.

In yet another aspect, the invention relates to a method of preventing or treating a disease or disorder, wherein inhibition of the production of pro-inflammatory cytokines and other inflammatory mediators, has a beneficial effect, comprising the step of administering to a subject in need thereof the fusion protein of the present invention in an amount effective to treat or prevent the disease or disorder.

In one embodiment such disease or disorder is an inflammatory disease mediated by the production of pro-inflammatory cytokines such as TNF, IL1$\beta$, IL6, chemokines such as IL8, and other inflammatory mediators.

According to one embodiment the fusion proteins taught herein can be used for inhibiting production and release of cytokines and other inflammatory mediators by cells, such as macrophages, monocytes, T-lymphocytes and other cells. As a result the fusion proteins of the present invention can be used for the preparation of a medicament for attenuating inflammatory reactions by inhibiting the release of cytokines and other inflammatory mediators by these cells in vivo. The fusion proteins of the present invention can be used as stand-alone drug or in combination with other drugs.

Treatment (prophylactic or therapeutic) may consist of administering the fusion protein of the present invention parenterally, preferably intravenously, intramuscularly, intrathecally, epidurally, spinally or subcutaneously. However, other administration routes as set forth above with respect to pharmaceutical compositions comprising the fusion proteins recited above may also be employed. The dose and administration regimen may depend on the extent of inhibition of the production and release of inflammatory cytokines aimed at. Typically, the amount of the fusion protein given will be in the range of 0.5 µg to 1 mg per kg of body weight. The dosage can be determined or adjusted by measuring the amount of circulating cytokine (IL10, IL4) upon administration in a biological sample.

For parenteral administration, the fusion protein is preferably formulated in an injectable form combined with a pharmaceutically acceptable parenteral vehicle. Such vehicles are well-known in the art and examples include saline, dextrose solution, Ringer's solution, and solutions containing small amounts of human serum albumin.

Typically, the fusion proteins of the present invention may be formulated in such vehicles at a concentration of from about 50 µg to about 100 mg per ml. In one embodiment of this invention the fusion protein is administered by intravenous injection.

Further administration details are set forth above in the section relating to pharmaceutical compositions comprising the fusion protein of the present invention.

Gene Therapy

The nucleic acid constructs or vectors of the present invention may be used as gene therapy agents for treatment of the conditions set forth above. In one embodiment of the invention, adeno-associated viruses are used as gene therapy vectors.

As such, an aspect the invention is directed to a gene therapy vector as described above for use in the prevention or treatment of OA, chronic pain, a condition characterized by local or systemic inflammation, immune activation, and/or lymphoproliferation, preferably wherein said condition characterized by local or systemic inflammation, immune activation, and/or lymphoproliferation is selected from the group consisting of: sepsis, adult respiratory distress syndrome, allo- and xenotransplantation, dermatitis, inflammatory bowel disease, sarcoidosis, allergies, psoriasis, ankylosing spondylarthitis, autoimmune diseases such as systemic lupus erythematosus and rheumatoid arthritis, glomerolonephritis, immune complex-induced and other forms of vasculitis, multiple sclerosis, Sjogren's disease, gout, lymphoproliferatieve diseases such as non Hodgkin lymphoma and B cell chronic lymphocytic leukemia, burn injuries, multiple trauma, stroke, myocardial infarction, atherosclerosis, diabetes mellitus, extracorporeal dialysis and blood oxygenation, ischemia-reperfusion injuries, and toxicity induced by the in vivo administration of cytokines or therapeutic monoclonal antibodies, chronic pain syndrome, and neuropathic and/or inflammatory pain.

The present invention will now be illustrated with reference to the following examples, which set forth particularly advantageous embodiments. However, it should be noted that these embodiments are illustrative and are not to be construed as restricting the invention in any way.

SEQUENCE LISTING

The instant application contains a Sequence Listing which has been filed electronically in ASCII format and is hereby incorporated by reference in its entirety. Said ASCII copy, created Dec. 9, 2019, is named 56780_701_302_SL.txt and is 6,058 bytes in size.

SEQ ID NO: 1
Amino acid sequence of IL4
HKCDITLQEIIKTLNSLTEQKTLCTELTVTDIFAASKNTTEKETFCRAAT

VLRQFYSHHEKDTRCLGATAQQFHRHKQLIRFLKRLDRNLWGLAGLNSCP

VKEANQSTLENFLERLKTIMREKYSKCSS

SEQ ID NO: 2
Amino acid sequence of IL10
SPGQGTQSENSCTHFPGNLPNMLRDLRDAFSRVKTFFQMKDQLDNLLLKE

SLLEDFKGYLGCQALSEMIQFYLEEVMPQAENQDPDIKAHVNSLGENLKT

-continued

LRLRLRRCHRFLPCENKSKAVEQVKNAFNKLQEKGIYKAMSEFDIFINYI

EAYMTMKIRN

SEQ ID NO: 3
Amino acid sequence of linker
GSGGGGSGT

SEQ ID NO: 4
Amino acid sequence of IL4-IL10 fusion protein
(the linker sequence is underlined; IL4 is
located N-terminal of IL10)
HKCDITLQEIIKTLNSLTEQKTLCTELTVTDIFAASKNTTEKETFCRAAT

VLRQFYSHHEKDTRCLGATAQQFHRHKQLIRFLKRLDRNLWGLAGLNSCP

VKEANQSTLENFLERLKTIMREKYSKCSS<u>GSGGGGSGT</u>SPGQGTQSENSC

THFPGNLPNMLRDLRDAFSRVKTFFQMKDQLDNLLLKESLLEDFKGYLGC

QALSEMIQFYLEEVMPQAENQDPDIKAHVNSLGENLKTLRLRLRRCHRFL

PCENKSKAVEQVKNAFNKLQEKGIYKAMSEFDIFINYIEAYMTMKIRN

BRIEF DESCRIPTION OF THE FIGURES RELATED TO THE INVENTION

FIG. 1 shows levels of IL4-IL10 fusion protein obtained from HEK293 cells transfected with IL4-IL10 fusion protein. Supernatant of HEK293 cells, which were transfected with a pUPE expression vector carrying the transgene for IL4-IL10 fusion protein, was tested in sandwich ELISA assays for IL4 (A) and IL10 (B), according to manufacturer's instructions. Results were expressed as optical density (OD) versus dilution of culture supernatant.

Figure 2:
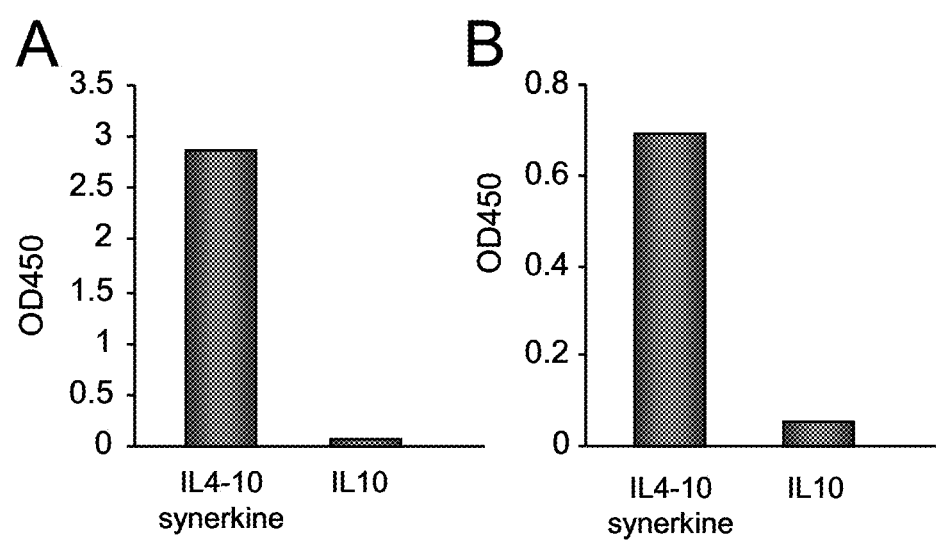

FIG. 2 shows the immunochemical identification of the IL4-IL10 fusion protein by cross-ELISA. Supernatant of HEK293 cells, which were transfected with a pUPE expression vector carrying the transgene for IL4-IL10 fusion protein, was tested in the cross-ELISA with anti-IL4 (A) or anti-IL10 monoclonal antibodies (used as capture antibodies) (B), and biotinylated anti-IL10 (A) or anti-IL4 (B) monoclonal antibodies (used as detecting antibodies). Recombinant IL10 was tested as a negative control. The results show that the IL4-IL10 protein can be detected via both its IL10 portion (panel A) and its IL4 portion (Panel B).

Figure 3:
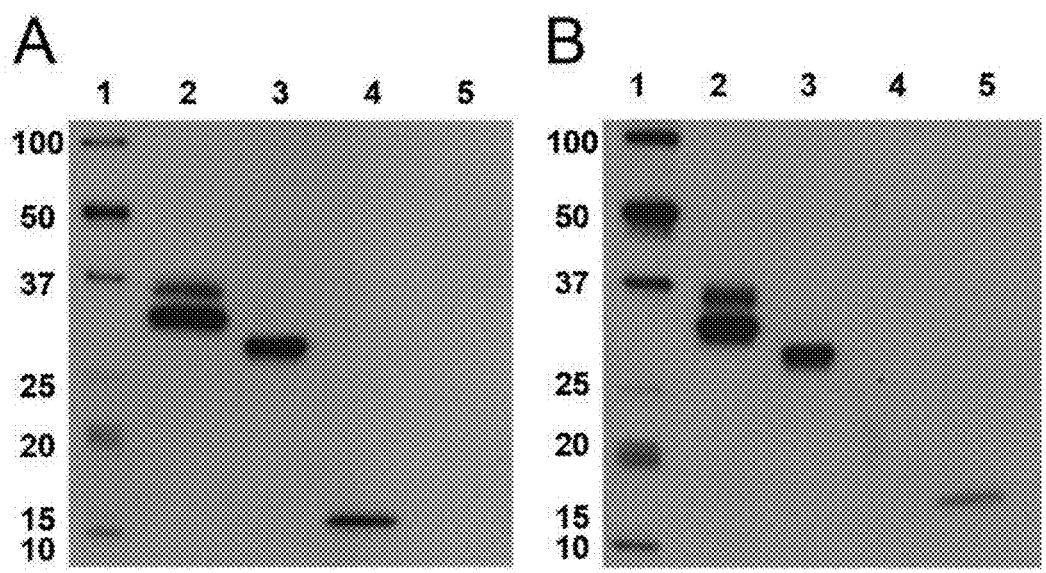

FIG. 3 shows Western blot identifying IL4-IL10 fusion protein in supernatant of HEK293 cells. A quantity of 10 microliters of supernatant obtained from HEK293 cells, which were transfected with cDNA coding for IL4-IL10 fusion protein, was run on SDS-PAGE. Blots were developed with labelled anti-IL4 antibodies (A) or with labelled anti-IL10 antibodies (B). As controls, recombinant IL4 and IL10 were used. Lane 1=molecular marker, Lane 2=untreated IL4-IL10 fusion protein, lane 3=deglycosylated IL4-IL10 fusion protein, lane 4=IL4, and lane 5=IL10.

Figure 4:
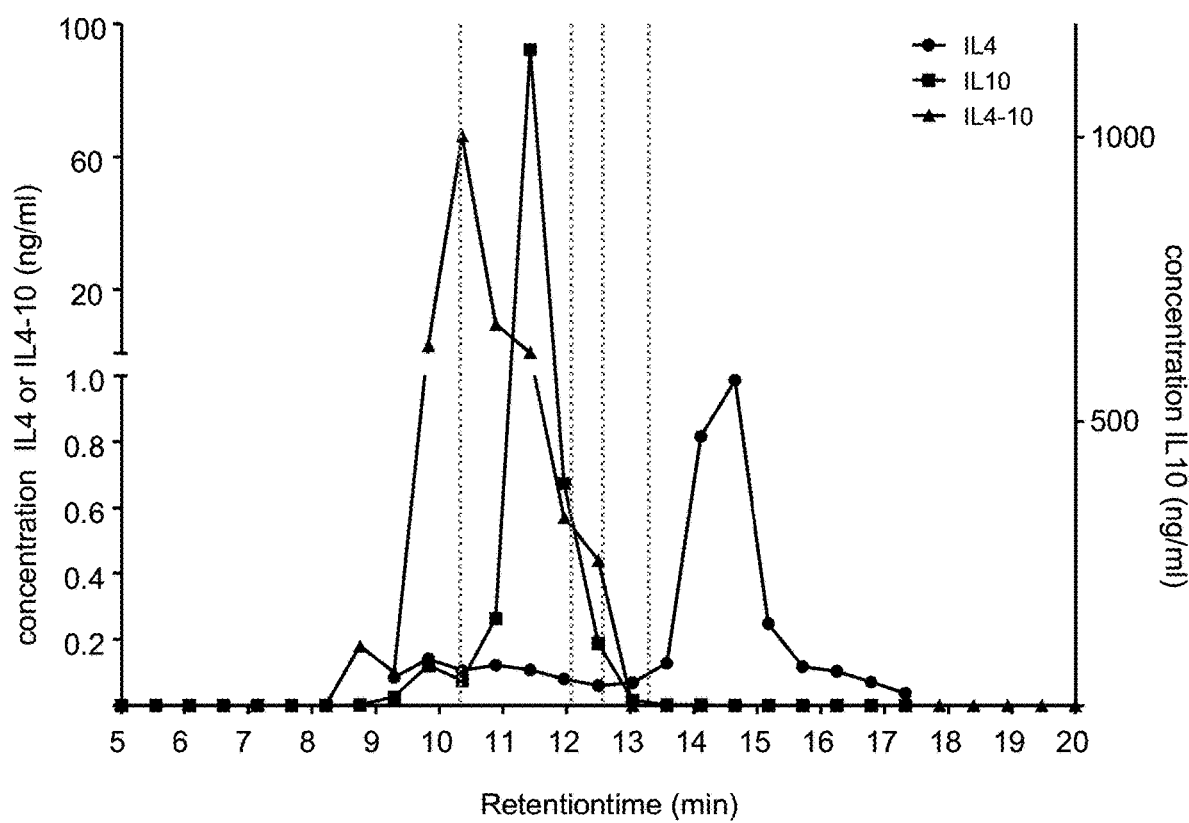

FIG. 4 displays the results from a High Performance Size Exclusion Chromatography assay identifying polymerisation of the IL4-IL10 fusion protein. Samples of the IL4-IL10 fusion protein, recombinant IL4, and recombinant IL10 were run on a High Performance Liquid Chromatography system. The column was calibrated using a protein mix of thyroglobulin, bovine serum albumen (66 KD, $1^{st}$ dotted line from left), carbonic anhydrase (30KD, $2^{nd}$ dotted line from left), myoglobulin (18 KD, $3^{rd}$ dotted line from left), and ribonuclease (13.7 KD, $4^{th}$ dotted line from left). Using these markers, the molecular weight of the proteins in the fractions was estimated by comparison of the retention times. IL4 and IL10 content in the fractions of the various runs was measured with ELISA and expressed as ng per ml. IL4 eluted as an apparent monomer, IL10 as an apparent dimer, whereas the elution pattern of IL4-IL10 fusion protein revealed an apparent dimer.

Figure 5:
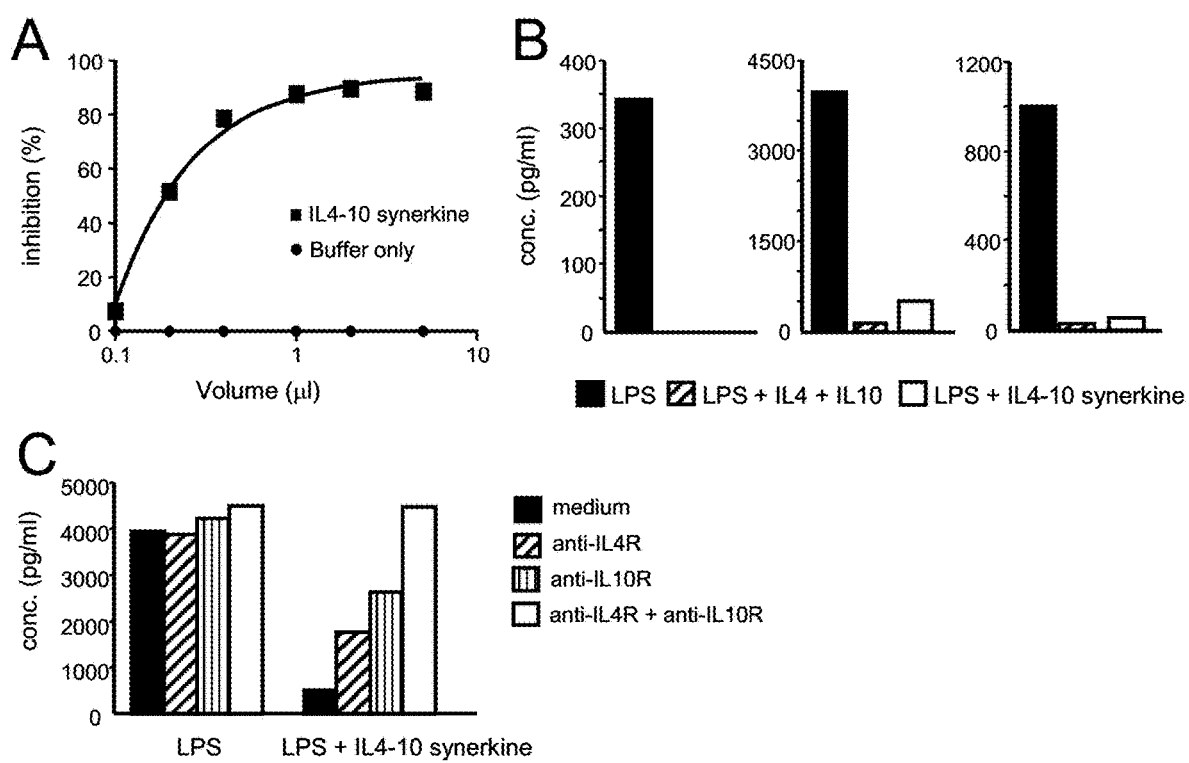

FIG. 5 shows that IL4-IL10 fusion protein inhibits LPS-induced cytokine release in whole blood cultures. Heparinized blood from healthy volunteers was diluted 1:10 in culture medium and incubated with LPS at a concentration of 10 ng/ml in the presence of various concentrations of the IL4-IL10 fusion protein. TNFα in the supernatants was measured with ELISA. Panel A shows the ability of IL4-IL10 fusion protein to inhibit production of TNF (results expressed as % inhibition). Note that no inhibition of TNF production was seen when a similar volume of culture medium lacking IL4-IL10 fusion protein was tested. Panel B shows inhibition of LPS-induced TNFα (left graph), IL6 (middle graph) and IL8 (right graph) production (concentrations TNFα, IL6 and IL8 measured from the supernatant is given in the Y axis). The IL4-IL10 fusion protein was tested at 100 ng/ml, and compared with the effect of a mixture of recombinant IL4 and IL10 at a final concentration of 50 ng/ml each. Panel C shows that the effect of the IL4-IL10 fusion protein on LPS-induced production of IL6 was completely abolished when receptor blocking antibodies against the IL4 receptor (anti-IL4R) and the IL10 receptor (anti-IL10R) were both added relative to when only medium (lacking antibodies) was added. Note that the effect of the IL4-IL10 fusion protein was only partially abolished when a receptor blocking antibody against either IL4 receptor (anti-IL4R) or the IL10 receptor (anti-IL10R) (but not both) was added.

Figure 6:
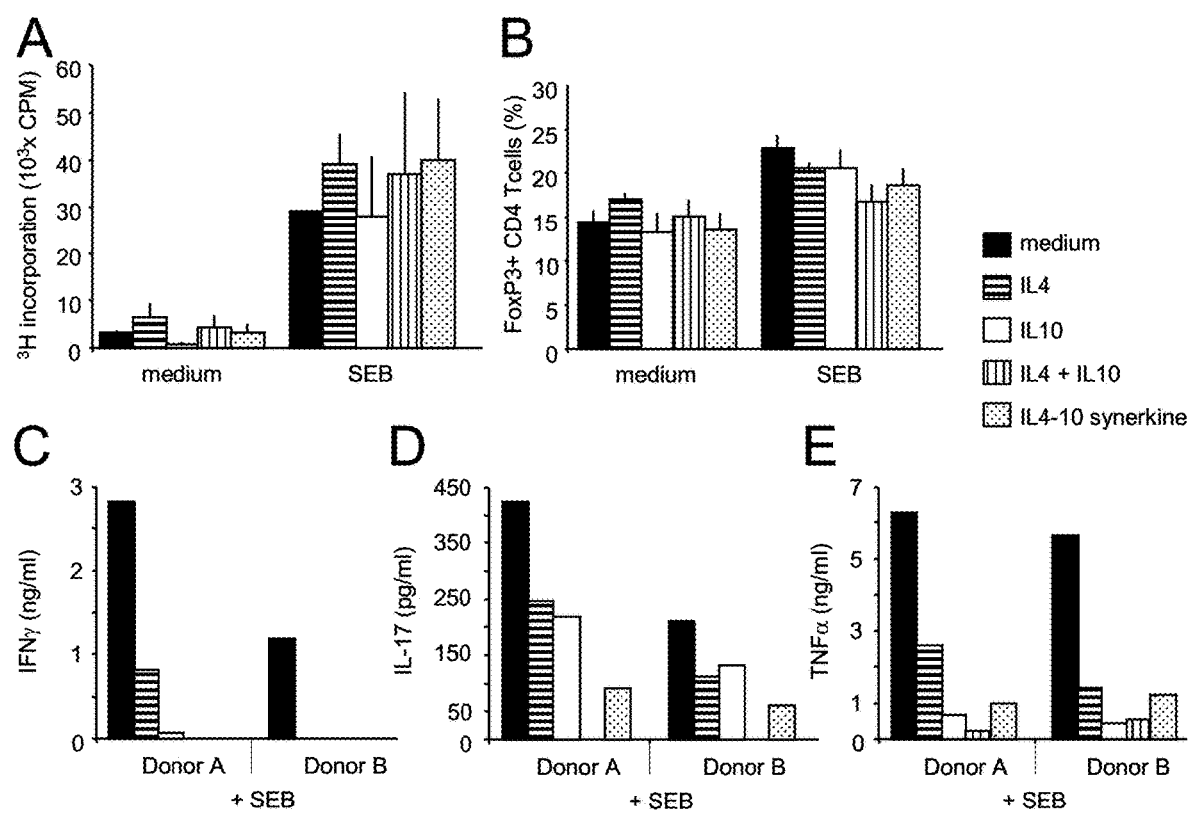

FIG. 6 shows the potent inhibition of Th1 and Th17 cytokine production by IL4-IL10 fusion protein is associated with sustained regulatory (FoxP3+) T-cell percentages in superantigen Staphylococcus enterotoxin B (SEB)-activated mononuclear cell cultures. Activation of myeloid cells and B cells is critically dependent on the balance of pro-inflammatory Th1 and Th17 and regulatory FoxP3-expressing CD4 T cells. To assess the effects of IL4-IL10 fusion protein on T cell activation, mononuclear cells from the peripheral blood (PBMC) of healthy donors were isolated. T cell activation was induced by treatment of PBMC ($5.10^5$/ml) for 3 days in the presence or absence of SEB (1 ng/ml) and/or IL4-IL10 fusion protein. Following SEB treatment, culture period proliferation (panel A), FoxP3 expression and pro-inflammatory T-cell cytokine production (panel B) were measured. SEB induced a significant proliferation associated (panel A) with upregulation of FoxP3 expression (panel B). Both proliferation (panel A) and FoxP3 expression (panel B) were hardly affected by IL4-10 fusion protein. By contrast, Th1 and Th17 cytokines IFNγ (left graph, panel C), IL17 (middle graph, panel C) and TNFα (right graph, panel C) were all strongly reduced by IL4-IL10 fusion protein. Together, this demonstrates that IL4-IL10 fusion protein strongly alters the balance between suppressive regulatory CD4 T cells and pro-inflammatory Th1 and Th17 cells.

Figure 7:
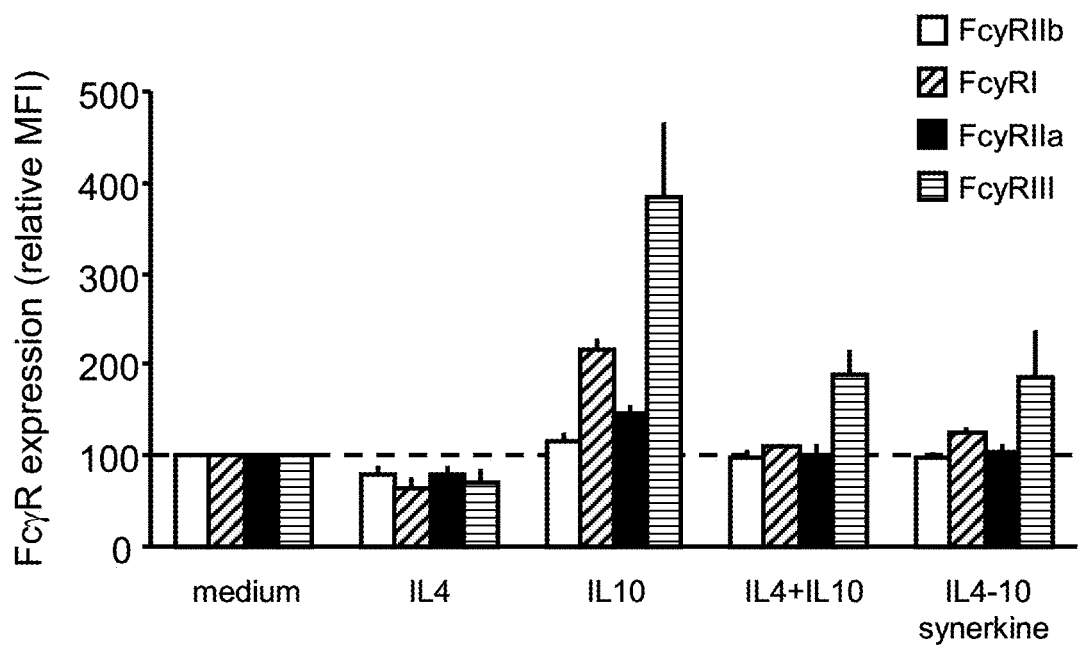

FIG. 7 shows the stabilization of expression of receptors for IgG on monocytes by IL4-IL10 fusion protein in Staphylococcus enterotoxin B (SEB)-activated mononuclear cell cultures. The balance between activating and inhibitory receptors for IgG (FcγRs) plays a pivotal role in immune complex-mediated activation of myeloid and lymphoid cells. To assess effects of IL4-IL10 fusion protein on FcγR expression on monocytes, mononuclear cells were isolated from a healthy donor. T-cell-dependent monocyte activation was induced by treatment of PBMC ($5.10^5$/ml) for 2 days in the presence or absence of the superantigen SEB (0.1 ng/ml) and/or IL4-IL10 fusion protein. After this culture period, FcγRs expression was measured. IL10 upregulated the expression of FcγRI, FcγRIIa, and FcγRIII. IL4 alone showed a slight decrease in the expression of these activating FcγRs as compared to cells cultured in the absence of cytokines. The combination of IL4 and IL10 and the IL4-IL10 fusion protein normalized expression of FcγRI and FcRγIIa. A slight increase by IL4 in combination with IL10 or IL4-IL10 fusion protein in FcγRIII expression was measured, although negligible compared to the induced upregulation of this receptor by IL10 alone. IL4 alone showed a slight decrease in the expression of FcγRIIb. The combination of IL4 with IL10, and IL4-IL10 fusion protein did not alter the expression of the inhibitory FcγRIIb. These results demonstrate that IL4-IL10 fusion protein stabilizes the expression of activating FcγRs, which in turn can inhibit immune complex-induced immune activation.

Figure 8:
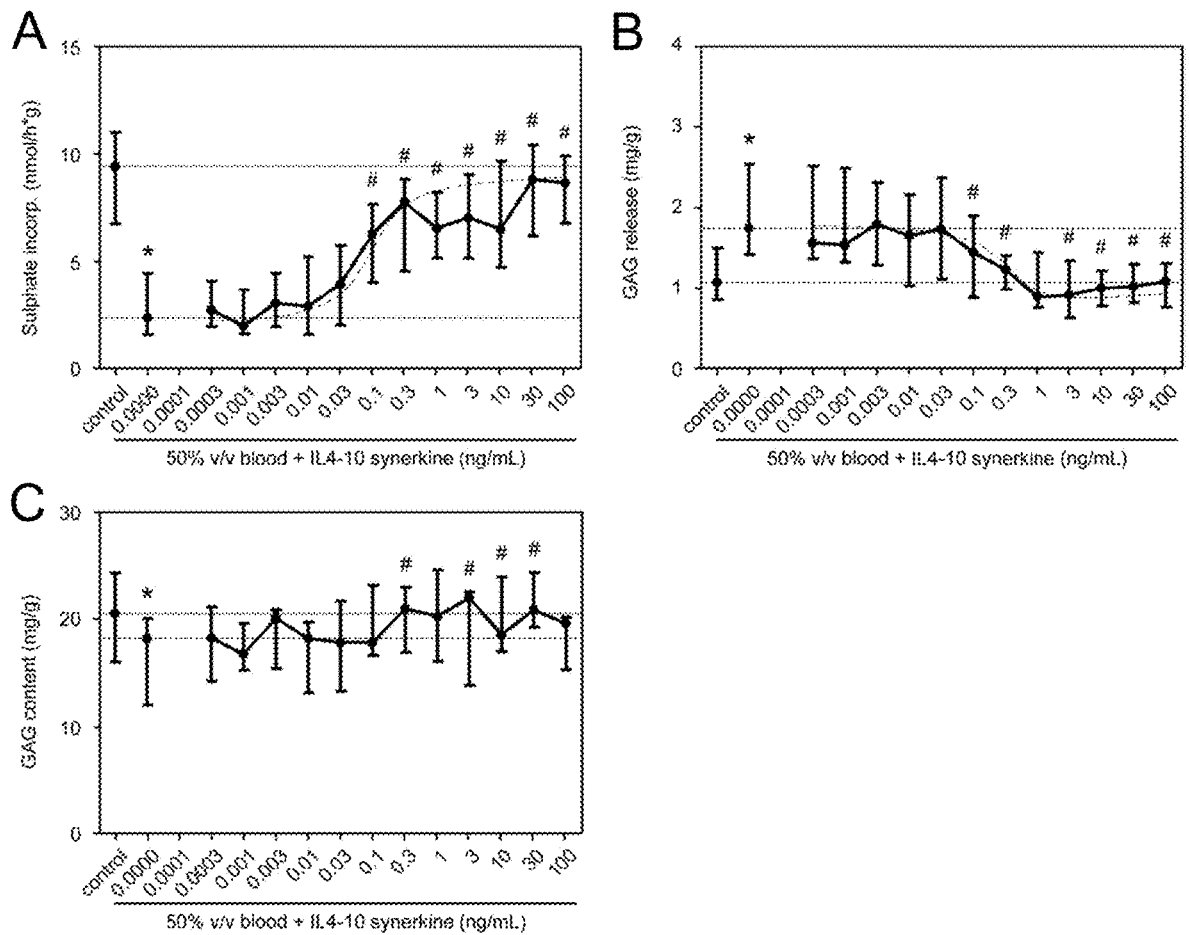

FIG. 8 shows a dose-response effect of the IL4-IL10 fusion protein on cartilage proteoglycan turnover. Cartilage explants of 5 donors were exposed for 4 days to 50% v/v blood of 5 donors (n=5). During blood exposure the IL4-IL10 fusion protein was added in a concentration of 0.0001 to 100 ng/mL. Proteoglycan synthesis rate (A), release (B), and content (C) were determined after a recovery period of 12 days. Proteoglycan synthesis rate and content were significantly decreased due to blood exposure when compared to control cartilage, while proteoglycan release was increased (indicated by asterisks; p<0.05). Hash tags indicate statistically significant differences compared to 50% v/v blood (p<0.05), while the dotted line in A and B emphasizes the sigmoid appearance of the dose-response. Median values ±interquartile ranges are depicted. Addition of the IL4-IL10 fusion protein to the cartilage cultures resulted in a dose-dependent recovery of proteoglycan synthesis rate; normalisation of proteoglycan release, and content decrease was counteracted.

Figure 9:
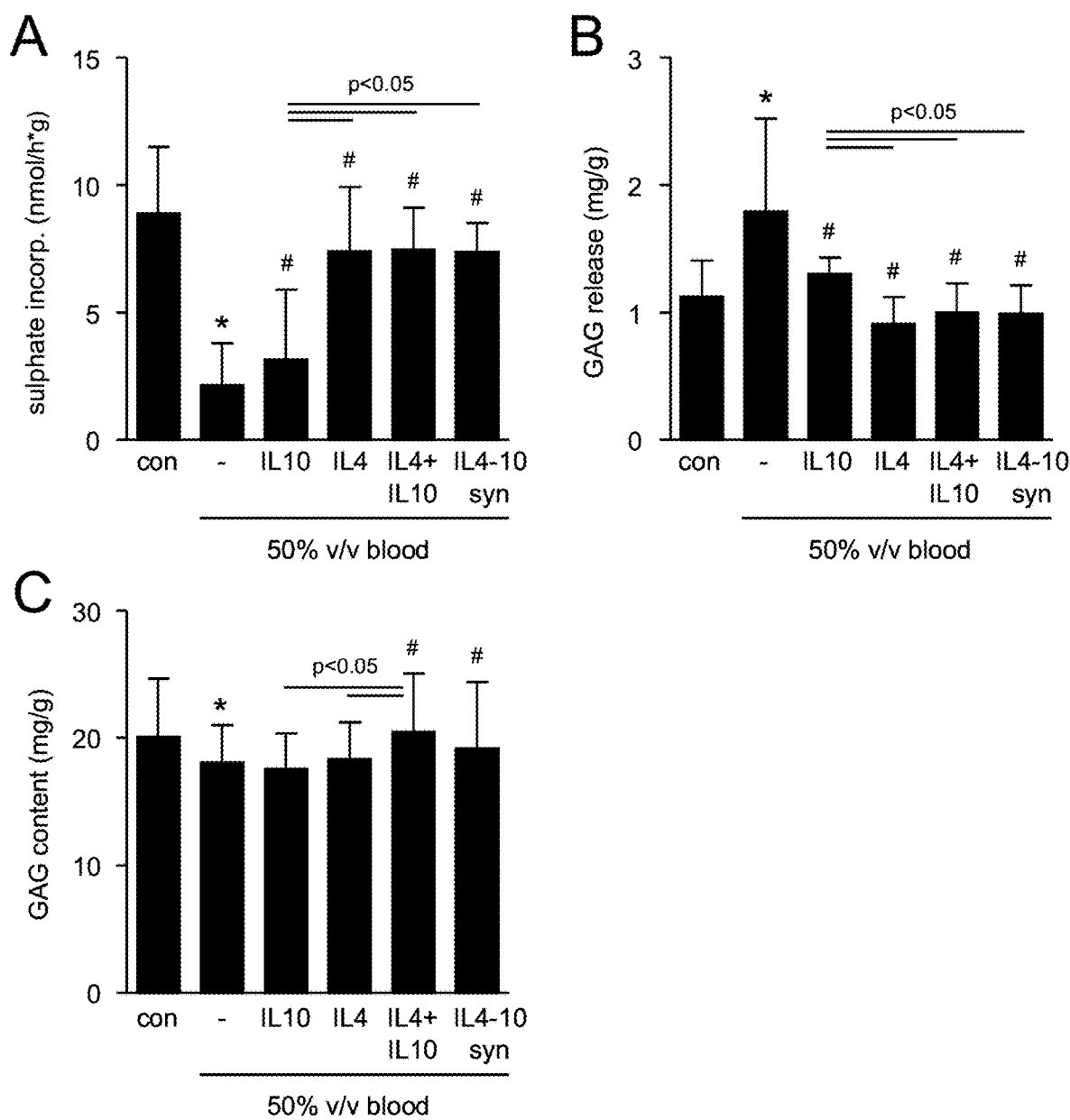

FIG. 9 shows that IL4-IL10 fusion protein prevents blood-induced cartilage damage. Cartilage explants of 8 donors were exposed for 4 days to 50% v/v blood of 8 donors. During blood exposure, the IL4-IL10 fusion protein as well as IL4, IL10, and the combination of IL4 with IL10 were added (all 10 ng/mL). Proteoglycan synthesis rate of the cartilage explants was decreased by 76% due to blood-exposure (A, p=0.012). IL4-IL10 fusion protein increased the proteoglycan synthesis rate with 241% as compared to blood-exposure alone. Blood-exposed cartilage showed 59% increase of proteoglycan release (B, p=0.017). Addition of IL4-IL10 fusion protein decreased blood-induced release of proteoglycans (p=0.012) back to control values. Cartilage exposed to blood showed a 10% decrease in proteoglycan content as compared to control (C, p=0.012). IL4-IL10 fusion protein significantly increased proteoglycan content compared to blood-exposure alone (p=0.012). The symbol * indicates statistically significant differences compared to control, The symbol # indicate statistically significant differences compared to 50% v/v blood (p<0.05). Median values±interquartile ranges are depicted.

Figure 10:
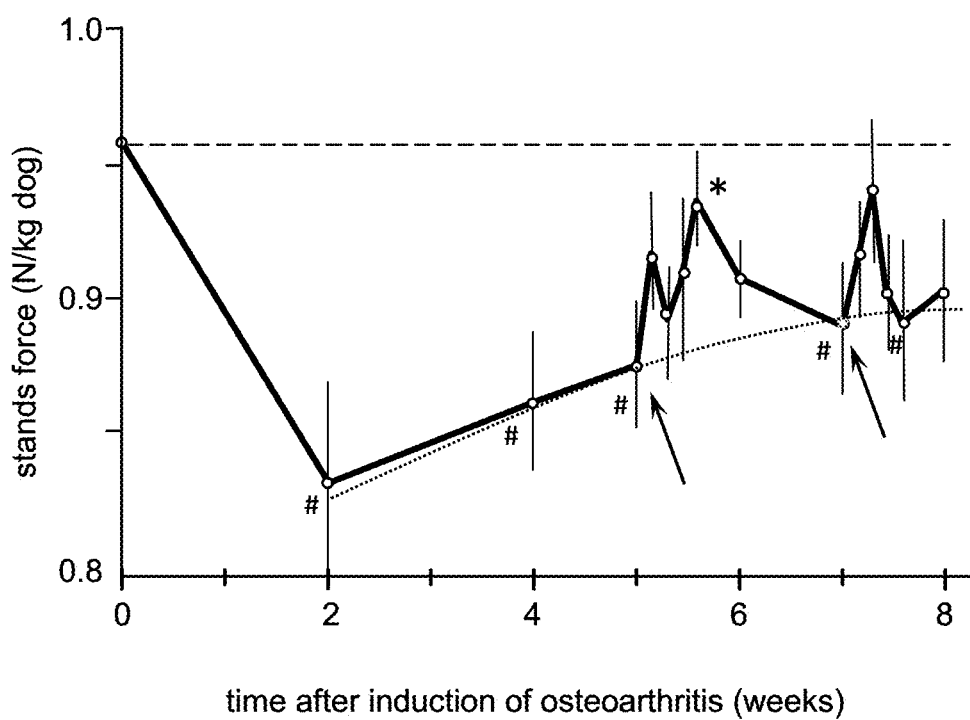

FIG. 10 shows that IL4-IL10 fusion protein reduces pain in the canine Groove-model for osteoarthritis (OA). OA was induced in 4 dogs, and intra-articular injections of 1 ml IL4-IL10 fusion protein were given at 5 weeks (1 µg/ml) and 7 weeks (101 µg/ml) after OA induction (see both arrows). Force-plate analysis (FPA) was performed every 2 weeks starting from 3 weeks before and ending at 8 weeks after induction, with additional daily FPA after the IL4-IL10 fusion protein injections. Loading of the OA joint (experimental joint vs. contra-lateral control joint) almost normalized compared to the level just before injection (2% vs. 9% inhibition compared to pre-OA loading respectively), indicated by a spike in the stand force. This effect on loading, indicative of pain relieve, was obtained over days after which loading dropped again. After the second injection in week 7, a change in unloading from 7% (compared to pre OA loading) to 2% compared to pre OA loading was reached. Thus, again a positive effect of IL4-IL10 fusion protein on the loading pattern of the affected OA joint and almost complete normalisation was established. The symbol * indicates p=0.05 compared to pre-injection value while the symbol # indicates p<0.05 compared to baseline value. The curved dotted line indicated the natural course of OA pain (unloading) without treatment.

Figure 11:
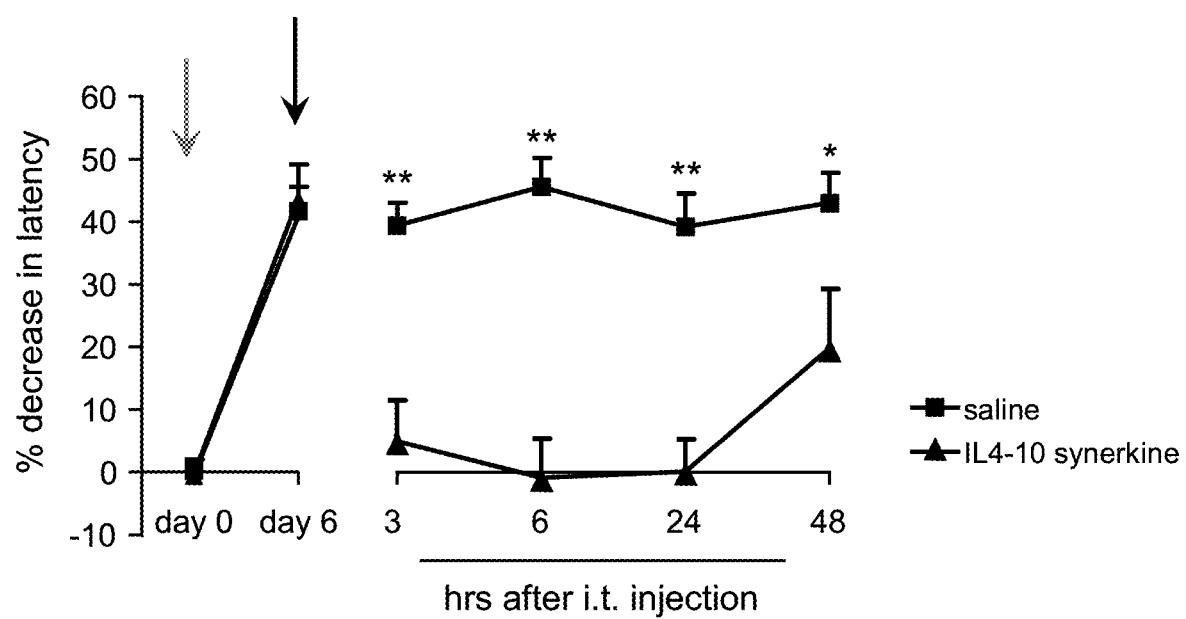

FIG. 11 shows the time course of carrageenan-induced thermal hyperalgesia in mice treated with IL4-IL10 fusion protein. Heat withdrawal latencies were determined using the Hargreaves test. Mice received an intraplantar injection of carrageenan (See first arrow from left), and the decrease in heat withdrawal latency was determined. Intrathecal injection with IL4-IL10 fusion protein (see second arrow from left) significantly reduced the hyperalgesic response to intraplantar carrageenan. The effect of IL4-IL10 fusion protein was less apparent after 2 days, although the decrease in heat withdrawal latency displayed by mice treated with IL4-IL10 fusion protein was still significantly smaller compared to saline-treated mice after 48 hours. Data are expressed as mean±SEM. The symbol * indicates p<0.05; the symbol ** indicates p<0.001.

Figure 12:
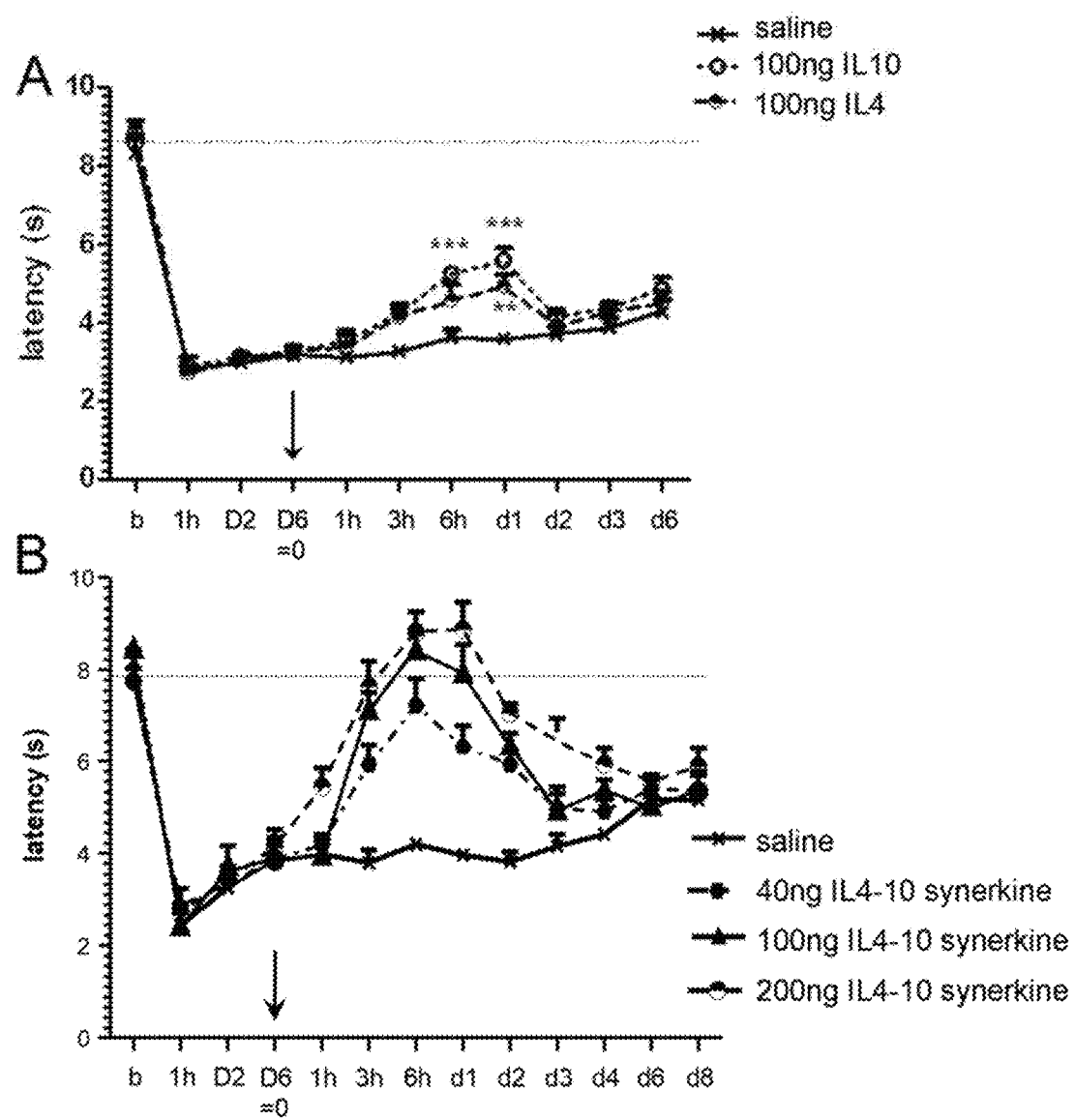

FIG. 12 shows the heat withdrawal latencies determined using the Hargreaves test. Mice received an intraplantar injection of carrageenan, and the decrease in heat withdrawal latency was determined. Intrathecal injections (see arrows) with either IL4 or IL10 (A) or IL4-IL10 fusion protein (B) were given at day 6 after hyperalgesia induction. Both IL4 and IL10 slightly reduced the hyperalgesic response to intraplantar carrageenan pain response but the effect of a combination of IL4 and IL10 was negligible compared to the effect of IL4-IL10 fusion protein. The effect of the separate IL4 or IL10 lasted for 1 day, whereas the effect of the IL4-IL10 fusion protein lasted for a much longer period, up to day 4. Data are expressed as mean±SEM. The symbol * indicates p<0.05; The symbol ** indicates p<0.001.

Figure 13:
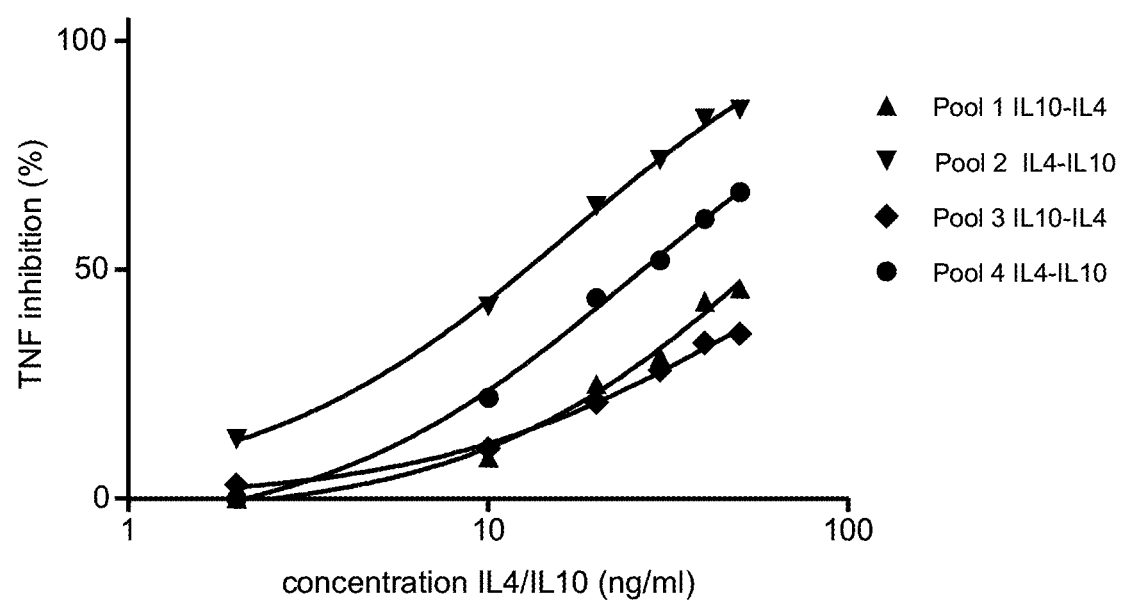

FIG. 13 shows that IL4-IL10 fusion protein inhibits LPS-induced cytokine release in whole blood cultures. Heparinized blood from healthy volunteers was diluted 1:10 in culture medium and incubated with LPS at a concentration of 10 ng/ml in the presence of various concentrations of the pools containing different constructs of IL4-IL10 fusion protein. TNFα in the supernatants was measured with ELISA. Results were expressed as % inhibition. TNF production in the absence of IL4-IL10 fusion protein resulted in 0% inhibition. Pools 2 and 4, where the IL4 c-terminus was linked to the n-terminus of IL10, showed the highest inhibition of TNFα production at similar concentrations compared to pools 1 and 3, where IL10 c-terminus was linked to the n-terminus of IL4. This indicates that functionality of the IL4-10 fusion protein is dependent on the way separate cytokines are linked within the IL4-IL10 fusion protein.

EXAMPLES

Example 1. Transfection of HEK293 Cells

Method:
HEK293 cells were transiently transfected according to standard procedures with a vector containing a transgene (Y Derocher et al., Nucleic Acids Research 2002, vol 30, no 2, e9). Briefly, the IL4-IL10 fusion protein insert was cloned in a pUPE expression vector, containing a cystatin signal sequence. HEK293E cells were then transfected with the pUPE expression vector containing the IL4-IL10 fusion protein of the present invention. At the same time cells were co-transfected with a vector carrying the transgene for beta-galactoside alpha-2,3-sialyltransferase 5 (SIAT 9) homo sapiens to optimize capping of the glycans with sialic acid. Cells were cultured in FreeStyle medium (Invitrogen) with 0.9% primatone and ~0.04%, v/v, fetal calf serum. Five days after transfection, the conditioned medium was collected by low-speed centrifugation, after which it was concentrated over a 10 kDa QuixStand hollow fibre cartridge (GE Healthcare) and diafiltrated against phosphate buffered saline (PBS).

Example 2. ELISA Assays for Immunochemical Detection of IL4-IL10 Fusion Protein, IL4 and IL10

Method:
The IL4 and IL10 content in culture supernatant or chromatography fractions was measured by ELISA (IL4 PeliPair ELISA Kit; Sanquin, Amsterdam, the Netherlands; Cat # M9314 or IL10 PeliPair ELISA Kit; Sanquin; Cat # M9310) according to manufacturer's instructions. Briefly, catching antibodies against IL4 or IL10 were diluted 1:200 in phosphate buffered saline, pH 7.4 (PBS) and coated overnight onto an ELISA plate. All subsequent steps were performed in PBS supplemented with 0.1%, w/v, Tween-20 (PBS-T). A dose response curve consisting of serial dilutions to yield a range of 100 to 2 pg/ml of recombinant IL4 or IL10 was tested. Bound antibodies were detected with streptavidine-poly-HRP (Sanquin) followed by incubation with TMB (3,3',5,5"-tetramethylbenzidine; Invitrogen, Carlsbad, Calif., USA; Cat # SB02). Reaction was stopped with 1M Sulphuric Acid (Chem Lab; Cat # CL05-2658-1000). Results of the ELISAs were compared with those of references curves of dilutions of recombinant IL4 and IL10 provided by the manufacturer.

A cross-ELISA that specifically detected IL4-IL10 fusion protein was made by using anti-IL4 coated plates and biotinylated anti-IL10 monoclonal antibody for the detection. The cross-ELISA was performed exactly the same as the ELISA for IL10 except that anti-IL4 coated plates were used instead of anti-IL10 coated plates. The anti-IL4 coated plates were prepared exactly as described for the IL4 ELISA. As there was no standard for this assay, the results are given as OD. A fixed amount of supernatant, which was equivalent to 75 pg/ml of control recombinant IL10 and IL4-IL10 fusion protein was tested in this IL4-L10 fusion protein specific cross-ELISA.

Results:
Detection of the IL4-IL10 fusion protein. Both ELISA assays (see FIG. 1 and FIG. 2) yielded dose-response curves of culture supernatant of the transfected HEK293 cells, indicating the presence of IL4 and IL10 proteins, which had a structural conformation that was recognized by the monoclonal antibodies used in the ELISAs (FIG. 1). The ELISAs (cross-Elisa) were then modified to specifically measure the IL4-IL10 fusion protein and not the recombinant wild-type cytokine molecules (see FIG. 2A and FIG. 2B). When an amount equivalent to 75 pg/ml of recombinant IL10 and IL4-IL10 fusion protein were tested in this cross-ELISA, only the IL4-IL10 fusion protein gave a signal, but not IL10 (FIG. 2A and FIG. 2B). Thus these results demonstrate that only the supernatant obtained from HEK293 cells transfected with the sequence of the IL4-IL10 fusion protein of the present invention, contained a protein in which IL4 and IL10 sequences had been linked to each other.

Example 3. SDS-Page and Western Blotting

Method:
Samples were diluted 1:1 in sample buffer (Tris-HCl pH 6.8, 25%, w/v, Glycerol, 2%, w/v, SDS, 0.01%, w/v, bromophenol blue; BioRad, Richmond, Va., USA, Cat #161-0737), containing 710 mM 2-mercaptoethanol and incubated for 10 minutes at 100° C. Subsequently, samples were loaded on a 7.5%, w/v, polyacrylamide Tris/Glycine Gel (Mini-PROTEAN TGX Precast Gels without SDS; BioRad, Cat #456-1023). The molecular weight markers (WesternC Standard, 250-10 kD; BioRad; Cat #161-0376) were run on a separate lane. Electroporesis was performed under reducing conditions, using a Tris/glycine/SDS buffer (BioRad; Cat #161-0732). To identify the IL4-IL10 fusion protein, immunoblotting with anti-IL4 or anti-IL10 antibodies was performed. Proteins were separated on SDS-PAGE as described above, and then transferred to a PVDF-membrane (BioRad; Cat #161-0277) by Western blotting, using a Tris/glycine buffer (BioRad; Cat #161-0734) at 100V for 1 hour.

After blotting, the membrane was incubated with PBS-T containing 4%, w/v, milk powder (Elk milk powder; Campina, Zaitbommel, the Netherlands) to block remaining binding sites. The PVDF membrane was then washed 3× in PBS-T and incubated with the primary antibody (mouse IgG1 anti-human IL4; Santa Cruz Biotechnology, Santa Cruz, Calif., USA; Cat # SC80093 or mouse IgG1 anti-human IL10; Santa Cruz; Cat # SC32815) in 1%, w/v, milk (dissolved in PBST) for 1 hour. After another wash step, the blot was incubated for 1 hour with the secondary antibody (horse-radish peroxidase (HRP)-conjugated goat anti-mouse IgG; Santa Cruz; Cat SC2005) and a WesternC Marker detecting antibody (StrepTactin-HRP; BioRad; Cat #161-0382) in PBST-1% milk. ECL solution (GE Healthcare, Diegem, Belgium, Cat # RPN2132) was added to the washed membrane, where after the membrane was transferred to a cassette and developed for up to 15 minutes using the Kodak Imager. To further characterize the IL4-IL10 fusion protein, the culture supernatant was also treated with PNGaseF (Sigma Aldrich, cat # G5166) according to the manufacturer's instructions, to deglysolate the IL4-IL10 fusion protein, and thereafter analysed on SDS-PAGE and immunoblot as described above.

Results:
Wild-type IL4 and IL10 both migrated with a relative migration (Mr) consistent with a MW<20kD (lanes 4 and 5 of the blots shown in FIG. 3A and FIG. 3B). From the supernatant obtained from transfected HEK293, the IL4-IL10 fusion protein migrated as a double band with a Mr compatible with a MW ~30-35 kD. Both bands were recognized by anti-IL4 (FIG. 3A) and by anti-IL10 monoclonal antibodies (FIG. 3B), and therefore both represent variants of IL4-IL10 fusion protein, presumably different glycoforms. Notably, no bands were detected that corresponded with Mr in the range of recombinant wild-type IL4 or IL10 (lanes 2 in FIG. 3A and FIG. 3B). These results confirm that only IL4-IL10 fusion protein and not the individual cytokines (i.e. IL4 and IL10) are detected in the supernatant of the transfected HEK293 cells. To confirm that the double band described in lane 2 of panels 3A and 3B are glycoforms, supernatant containing IL4-IL10 fusion protein was treated with PNGaseF for deglycosylation and was compared with untreated supernatant by immunoblot. The results show that only one band is detected following deglycosylation (see lanes 3 in both blots shown in FIG. 3A and FIG. 3B), which confirms that the double band seen in lane 2 of both blots (FIG. 2A and FIG. 2B) is indeed the IL4-IL10 fusion protein of the present invention, but in a glycosylated form.

Example 4. Gel Filtration of IL4-IL10 Fusion Protein-High Pressure Size Exclusion Chromatography (SEC)

Method:
To determine the molecular weight of the IL4-IL10 fusion protein, a High Performance Size Exclusion Chromatography (HP-SEC) assay was performed. The gel filtration (BioSuite 125 4 μm UHR SEC Column; Waters; Cat #186002161) was performed on a High-Performance Liquid Chromatography System (Shimadzu) with 50 mM phosphate buffer containing 0.5 M NaCl as mobile phase. The column was calibrated prior to the run using a protein mix of thyroglobulin, bovine serum albumen, carbonic anhydrase, myoglobulin, and ribonuclease. The IL4-IL10 fusion protein purified by cation exchange was obtained by pooling and concentrating the chromatography fractions with the highest IL4-IL10 fusion protein content (2 ml of pooled fractions was concentrated to 100 μl, containing 2 μg of IL4-IL10 fusion protein). Fifty μl of 20 μg/ml of pooled IL4-IL10 fusion protein was injected and ran trough the column at a flow rate of 0.35 ml/min and under a pressure of 35 bar. Fractions of 175 μl were collected and the IL4 and IL10 content was measured in the above described IL4 and IL10 ELISA (1/500 dilution). Similar runs with recombinant human IL4 (Sigma, Cat #14269) and recombinant human IL10 (Sigma, Cat #19276) were performed to compare the molecular size of the IL4-IL10 fusion protein with that of the wild-type cytokines.

Results:
The HP-SEC elution pattern of IL4 indicates that IL4 is present as a monomer (~15kD). The elution pattern of IL10 shows that this cytokine is present in a dimeric form (~40kD), which is the naturally occurring form of IL10 (Zdanov et al, Stucture 1995, 3:591-601). The pattern of IL4-IL10 fusion protein indicates that it is mostly present in a dimeric form (~70 kD) (FIG. 4).

Example 5. Assays for Measuring Pro-Inflammatory Cytokines

Method:
TNFα production was measured using a commercial ELISA (TNF-α Pelipair ELISA Kit; Sanquin, Amsterdam, the Netherlands; Cat # M9323) according to manufacturer's instructions. Briefly, plates were coated with anti-TNFα catching antibody diluted 1 to 150 in a carbonate/bi-carbonate buffer, pH 9.6, washed 3 times with PBS-T, and incubated with 2.5%, w/v, bovine serum albumin (BSA; Roche Applied Science, Mannheim, Germany, Cat #10735108001) in PBS to block any remaining binding sites on the plate. After another wash-step, the wells were incubated with samples diluted in PBS-T. A standard curve of recombinant TNF-α at concentrations of 200-1.56 pg/ml in PBS-T was tested for reference. The recombinant TNF-α was supplied with the kit. Finally bound TNF-α was detected by incubations with biotinylated anti-TNF-α and streptavidin-poly-HRP (Sanquin; Cat #2032), respectively, in PBS-T. Bound HRP was visualized with TMB (3,3'5,5'tetramethylbenzidine; Invitrogen; Cat # SB02). To complete the ELISA 1M Sulphuric Acid (Chem Lab; Cat # CL05-2658-1000) was added. Results were referred to those of the standard curve of recombinant TNFα and were expressed as pg/ml. Similar ELISA procedures were used to measure IL6 and IL8 (purchased from Sanquin) and IFNγ and IL17 (purchased from Biosource).

Example 6. Assays for Measuring IL4-IL10 Fusion Protein, IL4 and IL10 Activity

Method:

Lipopolysaccharide (LPS) induced cytokine release (IL6, IL8, TNFα) in whole blood was used as a functional assay for IL4 and IL10. Heparinized human blood was obtained from healthy volunteers and diluted 1 to 10 in RPMI 1640 culture medium (Glutamax; Invitrogen, Cat #61870010) supplemented with Pen/Strep (PAA Laboratories, Pasching, Austria; Cat # P11-013). LPS (Lipopolysaccharide; Sigma; Cat # L4391) was added to yield a final concentration of 10 ng/ml. The IL4-IL10 fusion protein was added at a final concentration of 100 ng/ml. As controls, recombinant human IL4 (Sigma, Cat #14269) and recombinant human IL10 (Sigma, Cat #19276) were added at a final concentration of 50 ng/ml each. To verify the activity of IL10 and IL4, receptor blocking antibodies against human IL4-receptor (a-hIL4-R; R&D Systems; Minneapolis, Minn., USA, Cat # MAB230) and human IL10-receptor (a-IL10-R, BioLegend, San Diego, Calif., USA, Cat #308807) were added at final concentrations of 10 µg/ml and 20 µg/ml, respectively. The whole blood culture was then incubated for 18 hours at 37° C., where after the supernatant was collected, stored at −80° C. until tested for cytokines.

Results:

Levels of TNFα present in the supernatants were measured with ELISA and expressed as % inhibition of TNFα (FIG. 5A). The results show that the IL4-IL10 fusion protein significantly inhibited TNFα production while TNFα production in the absence of IL4-IL10 fusion protein resulted in 0% inhibition (FIG. 5A). Inhibition of LPS-induced TNFα, IL6, and IL8 production by IL4-IL10 fusion protein, or a combination of IL4 and IL10, was also measured using ELISA assays (FIG. 5B). The concentrations of TNFα, IL6, and IL8 present in the supernatant are given in the Y-axis. The IL4-IL10 fusion protein was tested at 50 ng/ml, and compared with the effect of a mixture of recombinant human IL4 and IL10 at a final concentration of 25 ng/ml each. The results show that both IL4-IL10 fusion protein and the combination of IL4 and IL10 significantly inhibited LPS-induced production of TNF, IL6, and IL8 relative to control (i.e. medium without cytokines). The effect of the IL4-IL10 fusion protein on LPS-induced production of IL6 was completely abolished when receptor blocking antibodies against human IL4-receptor (a-hIL4-R) and against human IL-10-receptor (a-IL10-R) were both added relative to control situation (e.g. medium only). However, the effect of the IL4-IL10 fusion protein on LPS-induced production of IL6 was partially abolished when either one of the two moieties (i.e. IL4 or IL10) was blocked by a receptor blocking antibody against human IL4-receptor (a-hIL4-R) or against human IL-10-receptor (a-IL10-R), relative to control situation (e.g. medium only).

Example 7. Effect of IL4-IL10 Fusion Protein on the Balance of Pro-Inflammatory (Th1 and Th17 Cytokine-Expressing Cells) and Regulatory T-Cell Activity (FoxP3-Expressing CD4 T Cells)

Method:

Activation of myeloid cells and B cells is critically dependent on the T-cell balance of pro-inflammatory Th1 and Th17 and regulatory FoxP3-expressing CD4 T cells. To assess effects of IL4-IL10 fusion protein on T-cell cytokine production, mononuclear cells from peripheral blood (PBMC) were isolated from healthy donors. Briefly, blood was diluted 1:1 with RPMI 1640 medium (Gibco BRL, Life Technologies, Merelbeke, Belgium) containing penicillin (100 U/ml, Yamanouchi, Leiderdorp, The Netherlands), streptomycin (100 mg/ml, Fisiopharma, Milano, Italy), and glutamine (2 mM, Gibco BRL). PBMCs were isolated by Ficoll-Paque density gradient centrifugation (Pharmacia, Uppsala, Sweden). PBMC ($5.10^5$/ml) were cultured for 3 days 37° C. in RPMI/glutamax (Gibco BRL) with added penicillin (100 U/ml), streptomycin (100 mg/ml), and 10% pooled fetal calf serum (FCS, Gibco BRL). PBMC were cultured in the presence or absence of the superantigen *Staphylococcus* enterotoxin B (SEB, 1 ng/ml) and/or IL4-IL10 fusion protein. After this culture period the supernatant was collected, rendered cell-free and stored at −80° C. until tested for IFNγ, IL17 and TNFα by ELISA. In addition, cell proliferation was measured by 3H-Thymidine incorporation. 3H-thymidine was added (5 mCi/ml, NEN Life Science Products, Amsterdam, The Netherlands) to each well during the last 18 hours of the 3-day cell culture. After this culture period cells were harvested and 3H-thymidine incorporation was measured by liquid scintillation counting and was expressed in counts per minute (CPM). Also, intracellular FoxP3 staining was performed using an APC-conjugated rat anti-human FoxP3 staining set (eBioscience, San Diego, USA). For intracellular staining, an APC-labelled rat isotype control antibody was used (eBioscience). Percentages positive/negative cells were determined based on markers that were set using isotype controls. Cell acquisition was done using a FACScan flow cytometer and data were analyzed with FlowJo software, version 7.5 (Tree Star Inc., Oregon, USA).

The synergistic activity of IL4-IL10 fusion protein on the inhibitory Fcγ receptor (FcγRIIb) expression on monocytes was also tested. This was compared to regulation of activating FcγRI and FcγRIII. PBMC ($1.10^6$/ml) were cultured for 4 days at 37° C. in RPMI/glutamax (Gibco BRL) with added penicillin (100 U/ml), streptomycin (100 mg/ml), and 10% pooled human AB serum (Gibco BRL). PBMC were cultured in the presence or absence of the superantigen SEB (1 ng/ml) and/or IL4-IL10 fusion protein. After this culture period, expression of the FcγRs was assessed by FACS analysis. For FACS analysis monocytes were incubated with APC-labelled CD14 mAb, FITC-labelled anti-FcγRI and anti-FcgRIII mabs (Pharmingen), and FITC-labelled anti-FcgRIIb mab (2B6, Genmab, Utrecht, Netherlands). Cell acquisition was done using a FACScan flow cytometer and data were analysed with FlowJo software, version 7.5 (Tree Star Inc., Oregon, USA).

Results:

SEB induced a significant proliferation which was associated with upregulation of FoxP3 expression. Both proliferation and FoxP3 expression were hardly affected by the IL4-IL10 fusion protein (FIG. 6A and FIG. 6B, respectively). By contrast, Th1 and Th17 cytokines IFNγ (left graph), IL-17 (middle graph), and TNFα (right graph) were all strongly reduced by IL4-IL10 fusion protein and the combination of IL4 and IL10 (FIG. 6C). Taken together, these results demonstrate that the IL4-10 fusion protein of the present invention strongly alters the balance between suppressive regulatory CD4 T cells and pro-inflammatory Th1 and Th17 cells.

Example 8. Effect of IL4-IL10 Fusion Protein on the Balance of Activating Fcγ Receptor I and III and Inhibitory FcγRIIb by IL4-IL10 Fusion Protein, IL4, IL10, and Combination of IL4 and IL10

Method:

The balance between activating and inhibitory receptors for IgG (FcγRs) plays a pivotal role in immune complex-mediated activation of myeloid and lymphoid cells. To assess effects of IL4-IL10 fusion protein on FcγR expression on monocytes, mononuclear cells from peripheral blood (PBMC) were isolated from a healthy donor. T-cell-dependent monocyte activation was induced by treatment of PBMC ($5.10^5$/ml) for 2 days in the presence or absence of the superantigen *Staphylococcus* enterotoxin B (SEB) (0.1 ng/ml) and/or IL4-IL10 fusion protein. After this culture period, FcγR expression was measured.

Results:

IL10 upregulated the expression of FcγRI, FcγRIIa, and FcγRIII (FIG. 7), whereas IL4 under these conditions showed a slight decrease in the expression of these activating FcγRs as compared to cells cultured in the absence of cytokines. The combination of IL4 and IL10 and the IL4-IL10 fusion protein normalized expression of FcγRI and FcRγIIa. Although a slight increase in FcγRIII was seen by the combination of IL4 and IL10 and IL4-IL10 fusion protein, this was negligible compared to the induced upregulation of this receptor by IL10 alone. IL10 alone showed a slight increase in the expression of the inhibitory FcγRIIb, whereas IL4 alone showed a slight decrease in the expression of this receptor. The combination of IL4 and IL10, and IL4-IL10 fusion protein did not alter the expression of the inhibitory FcγRIIb (FIG. 7). Together, these results demonstrate that the IL4-IL10 fusion protein of the present invention stabilizes the expression of activating FcγRs, which in turn can inhibit immune complex-induced immune activation.

Example 9. Cartilage Cultures for Blood-Induced Cartilage Damage

Method:

Healthy human articular cartilage tissue was obtained post mortem from humeral heads within 24 hours after death of the donor, approved by the medical ethical regulations of the University Medical Centre Utrecht. The donors (n=8; mean age 69.8±8.7 years, 3 males and 5 females) had no known history of joint disorders. Full thickness slices of cartilage were cut aseptically from the humeral head, excluding the underlying bone, and kept in phosphate-buffered saline (PBS, pH 7.4). Within 1 hour after dissection, slices were cut in small full thickness cubic explants and weighted aseptically (range 5-15 mg, accuracy ±0.1 mg). The explants were cultured individually in a 96-wells round-bottomed microtiter plate (at 5% $CO_2$ in air, pH 7.4, 37° C., and 95% humidity). Culture medium consisted of Dulbecco's Modified Eagle's Medium (DMEM; Invitrogen) supplemented with glutamine (2 mM), penicillin (100 IU/mL), streptomycin sulphate (100 µg/mL; all PAA), ascorbic acid (85 µM; Sigma), and 10% heat inactivated pooled human male AB+ serum (Gemini Bioproducts).

For each experiment, fresh blood was drawn from healthy human donors (n=8, mean age 28.0±5.0 years, 2 males and 6 females) in a vacutainer tube (nr. 367895; Becton Dickinson). To mimic a human joint bleed, cartilage was exposed to 50% v/v whole blood for 4 days, which is considered to be the natural evacuation time of blood from the joint cavity. After blood exposure, cartilage explants were washed twice under culture conditions for 45 minutes to remove all additives and were cultured for an additional 12 days. Medium was refreshed every 4 days. In the first experimental set-up using cartilage and blood of 5 of the 8 donors, a dose-response curve of the IL4-IL10 fusion protein was made by adding the IL4-IL10 fusion protein during blood exposure in a concentration of 0.0001, 0.0003, 0.001, 0.003, 0.01, 0.03, 0.1, 0.3, 1, 3, 10, 30, and 100 ng/mL (n=5). In a separate experiment, the optimal concentration of 10 ng/mL IL4-IL10 fusion protein was compared to a similar concentration of the combination of IL10 plus IL4, as well as the individual components (each 10 ng/mL, n=8).

As a measure of proteoglycan synthesis rate, proteoglycans being one of the major cartilage matrix components, the sulphate incorporation rate into glycosaminoglycans (GAGs) was determined. At the end of each experiment 74 kBq $Na_2^{35}SO_4$ (NEX-041-H carrier free; DuPont) was added per well. After 4 hours of pulse labelling of the newly formed sulphated GAGs, cartilage samples were washed twice in cold PBS and stored at −20° C. Thawed samples were digested for 2 hours at 65° C. with 2% papain (Sigma). Proteoglycan synthesis rate was determined by precipitation of GAGs with 0.3M hexadecylpyridinium chloride monohydrate (CPC; Sigma) in 0.2M NaCl. The precipitate was dissolved in 3M NaCl and the amount of radioactivity was measured by liquid scintillation analysis. Radioactive counts were normalised to the specific activity of the medium, labelling time, and wet weight of cartilage. Results were expressed as nanomoles of sulphate incorporated per gram wet weight of cartilage tissue (nmol/h*g).

Proteoglycan content of each cartilage explant and release of proteoglycans into culture medium were established by staining and precipitation of GAGs with Alcian Blue (Sigma) in the papain digest of cartilage samples and in culture medium, respectively. Staining was quantified by absorptiometry at 620 nm using chondroitin sulphate (Sigma) as a reference. Results were expressed as mg GAG per wet weight of cartilage tissue (mg/g) and mg GAG released during 4 days per wet weight of tissue (mg/g), for content and release, respectively. Because of focal differences in composition and bioactivity of the cartilage, proteoglycan turnover parameters were determined of 10 cartilage explants of the same donor, obtained randomly and handled individually. The average of these 10 samples was taken as a representative value for that cartilage donor.

Results:

Exposure of cartilage to 50% v/v blood for 4 days strongly decreased proteoglycan synthesis rate by 74% (FIG. 8A; p=0.043). Addition of the IL4-IL10 fusion protein resulted in a dose-dependent recovery of proteoglycan synthesis rate, i.e., from 0.1 ng/mL IL4-IL10 fusion protein and onwards, a significant increase in proteoglycan synthesis rate was observed when compared to blood exposure without IL4-IL10 fusion protein (all p=0.043) (FIG. 8A). The increase of 62% in proteoglycan release due to blood exposure was (statistically) significantly reversed (restored to control levels) by addition of the IL4-IL10 fusion protein from 0.1 ng/mL and onwards (FIG. 8B, all p=0.043, except for 1 ng/mL, p=0.080). This resulted in normalisation of proteoglycan release that was no longer different form control cultures. Total proteoglycan content decreased by 11% when cartilage explants were exposed to blood (FIG. 8C; p=0.043). The decrease in content by blood exposure was counteracted by addition of the IL4-IL10 fusion protein at concentrations of 0.3 ng/mL and onwards (all p=0.043, except for 1 and 100 ng/ml, both p=0.080) (FIG. 8C).

To compare the effect of the IL4-IL10 fusion protein to the combination of the cytokines and the individual components, the IL4-IL10 fusion protein, IL4, IL10, and the combination of both (each 10 ng/mL) were tested in the same assay. Proteoglycan synthesis rate was decreased by 76% due to blood exposure (FIG. 9A; p=0.012). Both IL10 and IL4 statistically significantly increased synthesis rate when compared to blood (p=0.017 and p=0.012, respectively). IL4-IL10 fusion protein used in the same concentration also increased proteoglycan synthesis rate, and thus was as equally effective as the combination of the two individual cytokines (241% and 245%, respectively, compared to blood exposure). Also the effect of the IL4-IL10 fusion protein was statistically significantly better than the effect of IL10 alone (p=0.025). Proteoglycan synthesis rate of the cultures with the IL4-IL10 fusion protein, with the combination of both cytokines, and with IL4 alone were not significantly different from controls anymore. Complete recovery from the blood-induced inhibition of proteoglycan synthesis, namely normalisation, was obtained. Blood exposure of cartilage increased proteoglycan release with 59% (FIG. 9B; p=0.017). Addition of IL10 reduced this enhanced release (p=0.012 compared to blood). IL4, the combination of IL-4 and IL-10, and the IL4-IL10 fusion protein decreased the release to a greater degree when compared to blood exposure (all p=0.012). The IL4-IL10 fusion protein was more potent when compared to IL10 alone (p=0.012), and equally effective as the combination of the individual cytokines (p=0.611).

Cartilage exposed to blood showed a decrease in proteoglycan content by 10% (FIG. 9C; p=0.012). The individual cytokines IL4 and IL10 did not prevent this reduction in content (p=0.093 and p=0.327, respectively, when compared to blood exposure). However, the IL4-IL10 fusion protein (statistically) significantly increased proteoglycan content compared to blood exposure without additions (p=0.012).

Example 10. The Canine Groove-Model for Pain and Osteoarthritis

Method:

The effect IL4-IL10 fusion protein on pain and functional ability in the canine Groove-model for osteoarthritis. The characteristics of the Groove model reflect those of human OA, making it an appropriate model to study human OA. The Groove-model is distinctive in that the degenerative cartilage changes are progressive, ultimately resulting in OA while synovial inflammation diminishes over time. Because of this, evaluation of the direct effects of medication on cartilage degeneration and pain is less influenced by possible indirect effects on inflammation. Additionally, the model is distinctive because there is no permanent trigger causing joint damage, making the model more sensitive to treatment. A permanent trigger for joint damage, such as joint instability used in other (canine) models for OA will counteract the possible beneficial effects of treatment. Altogether, the Groove-model is suitable for testing the therapeutic effect of the IL4-IL10 fusion protein on cartilage damage and pain caused disability by OA. Pain and functional ability are credited as very important parameters in clinical osteoarthritis research, as these parameters, rather than structural changes, force patients to seek medical attention. In canine models, changes in braking, vertical stance, and propelling ground reaction forces indicators for pain and functional ability can be evaluated by force-plate analysis (FPA). Loading of a joint will be influenced by pain and functional ability, depending on the stage of the process of joint degeneration. In the first two weeks after OA induction a clear reduction in unloading is found, most likely caused by surgery-related pain. However, after 3 weeks there is a steadier unloading of the affected limb as a result of OA-related pain.

OA was induced in 4 Mongrels dogs (Mixed Breed, skeletally mature), in the right knee, according to the Groove model. Ten longitudinal and diagonal grooves, depth 0.5 mm, were made on the weight-bearing parts of the femoral condyles. Bleeding and soft tissue damage was prevented as much as possible to prevent dominance of an inflammatory component contrasting inflammatory driven models and specific arthritis models. After surgery, synovium, fasciae and skin were sutured. The contralateral unoperated knee served as a control. Intra-articular injection of 1 ml IL4-IL10 fusion protein (1 ug/ml) was given at 5 weeks after OA induction (see first arrow from the left). Two weeks after the first injection (week 7) a second injection of a higher dosage (10 ug/ml) was given (see second arrow from the left).

Ground gait pattern, taken as a measure for pain and functional ability, was evaluated by force plate analysis (FPA). In canine models longitudinal changes in braking, vertical stance, and propelling reaction forces (GRFs) can be evaluated for each leg by FPA. A force-plate (FP), mounted flush with the surface of an 11 m walkway sampled (100 Hz) peak GRFs. Forces were normalized by body weight and time, and expressed in N/kg. A single handler guided the dogs by leash over the FP, at a walking pace, at a constant speed (1±0.2 m/s). A successful run consisted of sequential, distinct paw strikes of the right front and hind paw or the left front and hind paw, respectively. Ten valid runs were collected for each side of the dog and GRFs were averaged for each of the four legs. FPA was performed every 2 weeks starting from 3 weeks before and ending at 8 weeks after induction. Additional daily FPA was done after injections with IL4-IL10 fusion protein (week 5 and 7).

Results:

The results show that following the first IL4-IL10 fusion protein injection, loading of the OA joint (experimental joint vs. contralateral control joint) almost normalized (2% inhibition compared to pre OA loading) compared to the level just before injection (9% inhibition compared to pre OA loading) as indicated by an spike in the stand force (FIG. 10). The effect on loading, which is indicative of pain relieve, was obtained over days after which loading dropped again. After the second injection in week 7, a positive effect of IL4-IL10 fusion protein was also seen on the loading pattern of the affected OA joint. This was shown by a change in unloading from 7% (compared to pre OA loading) to 2% compared to pre OA loading, again almost complete normalisation. IL4-IL10 fusion protein was therefore able to reduce pain in this canine model for OA.

Example 11. The Canine Groove-Model for Pain and Osteoarthritis

Method:

OA is induced in Mongrels dogs (Mixed Breed, skeletally mature), in the right knee, according to the Groove model. Ten longitudinal and diagonal grooves, depth 0.5 mm, are made on the weight-bearing parts of the femoral condyles. Bleeding and soft tissue damage is prevented as much as possible to prevent dominance of an inflammatory component contrasting inflammatory driven models and specific arthritis models. After surgery, synovium, fasciae and skin are sutured. The contralateral unoperated knee serves as a control. The dogs are divided in two groups. The first group receives an intra-articular injection of IL4-IL10 fusion protein 5 weeks after OA induction. The second group receives an intra-articular injection of both IL4 and IL10 but in a free form, 5 weeks after OA induction. Two weeks after the first injection (week 7), a second injection of a higher dosage was given in the first group (10 ug/ml of IL4-IL10 fusion protein) and second group (5 ug/ml of IL4 and 5 ug/ml of IL10).

Ground gait pattern, taken as a measure for pain and functional ability, is evaluated by force plate analysis (FPA). In canine models longitudinal changes in braking, vertical stance, and propelling reaction forces (GRFs) can be evaluated for each leg by FPA. A force-plate, mounted flush with the surface of an 11 m walkway sampled (100 Hz) peak GRFs. Forces are normalized by body weight and time, and expressed in N/kg. A single handler guided the dogs by leash over the FP, at a walking pace, at a constant speed ($1\pm0.2$ m/s). A successful run consists of sequential, distinct paw strikes of the right front and hind paw or the left front and hind paw, respectively. Ten valid runs are collected for each side of the dog and GRFs are averaged for each of the four legs. FPA is performed every 2 weeks starting from 3 weeks before and ending at 8 weeks after induction. In both groups, additional daily FPA are done after injection with IL4-IL10 fusion protein (group 1) and injection with IL4 and IL10 in a free form (group 2), on both week 5 and week 7.

Results:

The results show that following both injections (week 5 and week 7), treatments with either the IL4-IL10 fusion protein (group 1) or the combination of IL4 and IL10 in a free form (group 2), produce positive effects on the loading patterns of the affected OA joint. However, much greater improvements in loading patterns of the affected OA joint are observed in response to treatment with the IL4-IL10 fusion protein relative to treatment with the combination of IL4 and IL10 in a free form, both on week 5 and week 7. It is also observed that the effects of the treatment with the IL4-IL10 fusion protein are more enduring over time than the effects of the treatment with a combination of IL4 and IL10 in a free form. Therefore, the IL4-IL10 fusion protein of the present invention is able to reduce pain in the canine model for OA to a much greater extent than what is achieved with the combination of IL4 and IL10 in a free form.

Example 12. The Murine Carrageenan-Induced Model for Hyperalgesia

Method:

Hyperalgesia was induced in female C57BL/6 mice by an intraplantar injection in the hind paw of 5 µl λ-carrageenan (2% w/v; Sigma-Aldrich, St. Louis, Mo., USA) diluted in saline at day 0 (see first arrow from left in FIG. 11). Intraplantar injection of saline alone did not induce detectable hyperalgesia. Responses to infrared heat stimulus, measured as the latency to withdraw the paw, were determined using the Hargreaves test (IITC Life Science, Woodland Hills, Calif.). Intensity of the light beam was chosen to induce a heat withdrawal latency time of approximately 8 seconds at baseline. Baseline withdrawal latencies were determined on three consecutive days. Mice developed hyperalgesia as evidenced by a decrease in withdrawal latency that lasted at least 10 days after the carrageenan injection. At day 6 the mice received a single intrathecal injection of either IL4 (100 ng), IL10 (100 ng), or IL4-IL10 fusion protein (40, 100, and 200 ng), or vehicle (saline) (see arrows in FIG. 11 and FIG. 12).

Results:

Mice show hyperalgesia, up to 6 days after carrageenan injection, indicated by a decrease in withdrawal latency (FIG. 11). At day 6 the mice received a single intrathecal injections of either 100 ng IL4-IL10 fusion protein (n=4) or saline (n=4) as a control. After IL4-IL10 fusion protein injection, hyperalgesia was inhibited as evidenced by a reduction in paw withdrawal latency values back to baseline (FIG. 11). The effect of a single dosage of IL4-IL10 fusion protein lasted up to 2 days. After 48 hours the effect was decreasing, but still significantly different from the % decrease in latency in control saline treated mice (FIG. 11).

In a complementary experiment using the same methodology as described above, carrageenan-induced thermal hyperalgesia was also assessed in mice treated with IL4, or IL10, or IL4-IL10 fusion protein. Specifically, intrathecal injections with either IL4 or IL10 (A) or IL4-IL10 fusion protein (B) were given at day 6 after hyperalgesia induction (FIG. 12). Although both IL4 and IL10 slightly reduced the hyperalgesic response to intraplantar carrageenan pain response, this effect was negligible compared to the superior effect of IL4-IL10 fusion protein (FIG. 12). Remarkably, the effect of the separate cytokines, i.e., IL4 or IL10 lasted for 1 day, whereas the effect of the IL4-IL10 fusion protein persisted for a much longer period, i.e. up to day 4 (FIG. 12B).

Example 13: Murine Carrageenan-Induced Model for Hyperalgesia

Method:

Hyperalgesia is induced in female C57BL/6 mice by an intraplantar injection in the hind paw of 5 µl λ-carrageenan (2% w/v; Sigma-Aldrich, St. Louis, Mo., USA) diluted in saline at day 0. Intraplantar injection of saline alone does not induce detectable hyperalgesia. Responses to infrared heat stimulus, measured as the latency to withdraw the paw, are determined using the Hargreaves test (IITC Life Science, Woodland Hills, Calif.). Intensity of the light beam is chosen to induce a heat withdrawal latency time of approximately 8 seconds at baseline. Baseline withdrawal latencies are determined on three consecutive days. Mice develop hyperalgesia as evidenced by a decrease in withdrawal latency that lasts at least 10 days after the carrageenan injection. At day 6 the mice receive a single intrathecal injection of either IL4-IL10 fusion protein (40, 100, and 200 ng), or solution containing a combination of IL4 (100 ng) and IL10 (100 ng) in a free form, or vehicle (saline).

Results:

The results show that, relative to the control situation (vehicle treatment), treatment with either the IL4-IL10 fusion protein or a combination of IL4 and IL10 in a free form, produce significant decrease in hyperalgesia. However, it is observed that treatment with the IL4-IL10 fusion protein exerts much greater inhibitory effects on hyperalgesia than the treatment based on the combination of IL4 and IL10 in a free form. It is also observed that the effects of a single dosage of IL4-IL10 fusion protein on hyperalgesia endure to a much greater extend over time that the effects of an equivalent dosage of the individual cytokines (i.e., combination of IL4 and IL10 in a free form).

Example 14. IL4-IL10 Fusion Protein Activity on LPS Induced TNF Production in a Whole Blood Culture Method:

Lipopolysaccharide (LPS) induced cytokine release (TNFα) in whole blood was used as a functional assay for IL4-IL10 fusion protein activity. Heparinized human blood was obtained from healthy volunteers and diluted 1 to 10 in RPMI 1640 culture medium (Glutamax; Invitrogen, Cat #61870010) supplemented with Pen/Strep (PAA Laboratories, Pasching, Austria; Cat # P11-013). LPS (Lipopolysacchande; Sigma; Cat # L4391) was added to yield a final concentration of 10 ng/ml. Four different pools containing different IL4-IL10 fusion protein constructs were tested. The differences between the pools lies in the way IL4 was linked to IL10 (e.g. IL4 c-terminal linked to n-terminal IL10 or vice versa). The different constructs were added at a final concentration of 2, 10, 20, 30, 40, and 50 ng/ml. The whole blood culture was then incubated for 18 hours at 37° C., where after the supernatant was collected, stored at −80° C. until tested for TNFα content. TNFα levels in the supernatants were measured using an ELISA assay (as described above in examples 2 and 5).

Results:

The results are shown as % inhibition of TNFα production. In the absence of IL4-IL10 fusion protein, no inhibition of TNFα production was observed. Pools 2 and 4, where the IL4 c-terminus is linked to the n-terminus of IL10, showed to highest inhibition of TNFα production compared to pools 1 and 3, where IL10 c-terminus is linked to the n-terminus of IL4 (used at the same concentration). These results indicate that functionality of the IL4-IL10 fusion protein is dependent on the way separate cytokines are linked within the IL4-IL10 fusion protein.

The invention claimed is:

1. A fusion protein consisting of, from N- to C-terminus, an IL-4, a linker, and an IL-10; or from N- to C-terminus, the IL-10, the linker, and the IL-4; wherein the IL-4 consists of an amino acid sequence with at least 99% sequence identity to SEQ ID NO: 1, the linker consists of the amino acid sequence of SEQ ID NO: 3, and the IL-10 consists of an amino acid sequence with at least 99% sequence identity to SEQ ID NO: 2, wherein the fusion protein inhibits production of TNFα, IL6, or a combination thereof by human cells as determined by a lipopolysaccharide stimulated cytokine release assay.

2. The fusion protein of claim 1, wherein the IL-4 amino acid sequence is SEQ ID NO: 1 and the IL-10 amino acid sequence is SEQ ID NO: 2.

3. The fusion protein of claim 1, wherein the fusion protein consists of, from N- to C-terminus, the IL-4, the linker, and the IL-10.

4. The fusion protein of claim 1, wherein the fusion protein consists of, from N- to C-terminus, the IL-10, the linker, and the IL-4.

5. The fusion protein of claim 1, wherein the fusion protein comprises one or more chemical modifications selected from the group consisting of glycosylation, fucosylation, sialylation, and pegylation.

6. The fusion protein of claim 1, wherein the fusion protein is in a monomeric form.

7. The fusion protein of claim 1, wherein the fusion protein is in a dimeric form.

8. A pharmaceutical composition comprising the fusion protein of claim 1 and a pharmaceutically-acceptable excipient, carrier, or diluent.

9. The pharmaceutical composition of claim 8, wherein the pharmaceutical composition is in a unit dosage form.

10. A sterile solution comprising the fusion protein of claim 1 and a pharmaceutically-acceptable parenteral vehicle, wherein the sterile solution is formulated for subcutaneous, intracapsular, intraarticular, intravenous, intrathecal, subarachnoid, or epidural administration.

11. The sterile solution of claim 10, wherein the fusion protein is present in the sterile solution at a concentration of between 50 μg and 100 mg per mL.

12. The sterile solution of claim 10, further comprising an isotonicity agent, saline, Ringer's solution, dextrose solution, or Hank's solution.

13. The sterile solution of claim 10, further comprising a preservative, an antibacterial agent, an antifungal agent, or a combination thereof.

14. The sterile solution of claim 10, further comprising water, ethanol, glycerol, propylene glycol, polyethylene glycol, vegetable oil, olive oil, ethyl oleate, monostearate salt, gelatin, lecithin, a surfactant, a coating material, or a combination thereof.

15. The sterile solution of claim 10, further comprising a biocompatible polymer selected from the group consisting of ethylene vinyl acetate, polyanhydrides, polyglycolic acid, collagen, polyorthoesters, and polylactic acid.

16. A sterile powder for preparation of a solution for parenteral administration, comprising the fusion protein of claim 1 and a pharmaceutically acceptable excipient.

17. The sterile powder of claim 16, further comprising lecithin, a surfactant, a coating material, or a combination thereof.

18. The sterile powder of claim 16, further comprising a biocompatible polymer selected from the group consisting of ethylene vinyl acetate, polyanhydrides, polyglycolic acid, collagen, polyorthoesters, and polylactic acid.

19. The sterile powder of claim 16, wherein the fusion protein comprises one or more chemical modifications selected from the group consisting of glycosylation, fucosylation, sialylation, and pegylation.

20. The sterile powder of claim 16, wherein the IL-4 amino acid sequence is SEQ ID NO: 1 and the IL-10 amino acid sequence is SEQ ID NO: 2.

21. A method of treating pain in a subject in need thereof, comprising administering to the subject an effective amount of the fusion protein of claim 1.

22. A method of treating inflammation in a subject in need thereof, comprising administering to the subject an effective amount of the fusion protein of claim 1.

23. A fusion protein that comprises IL-4 and IL-10, wherein the fusion protein comprises an amino acid sequence with at least 99% sequence identity to SEQ ID NO: 4; and wherein the IL-4 and the IL-10 are linked by a linker consisting of the amino acid sequence of SEQ ID NO: 3, wherein the fusion protein inhibits production of TNFα, IL6, or a combination thereof by human cells as determined by a lipopolysaccharide stimulated cytokine release assay.

24. The fusion protein of claim 23, wherein the fusion protein comprises the amino acid sequence of SEQ ID NO: 4.

25. The fusion protein of claim 23, wherein the fusion protein consists essentially of the amino acid sequence of SEQ ID NO: 4.

26. The fusion protein of claim 23, wherein the fusion protein consists of the amino acid sequence of SEQ ID NO: 4.

* * * * *

SEQUENCE LISTING

```
<160> NUMBER OF SEQ ID NOS: 4

<210> SEQ ID NO 1
<211> LENGTH: 129
<212> TYPE: PRT
<213> ORGANISM: homo sapiens

<400> SEQUENCE: 1

His Lys Cys Asp Ile Thr Leu Gln Glu Ile Ile Lys Thr Leu Asn Ser
1               5                   10                  15

Leu Thr Glu Gln Lys Thr Leu Cys Thr Glu Leu Thr Val Thr Asp Ile
            20                  25                  30

Phe Ala Ala Ser Lys Asn Thr Thr Glu Lys Glu Thr Phe Cys Arg Ala
        35                  40                  45

Ala Thr Val Leu Arg Gln Phe Tyr Ser His His Glu Lys Asp Thr Arg
    50                  55                  60

Cys Leu Gly Ala Thr Ala Gln Gln Phe His Arg His Lys Gln Leu Ile
65                  70                  75                  80

Arg Phe Leu Lys Arg Leu Asp Arg Asn Leu Trp Gly Leu Ala Gly Leu
                85                  90                  95

Asn Ser Cys Pro Val Lys Glu Ala Asn Gln Ser Thr Leu Glu Asn Phe
            100                 105                 110

Leu Glu Arg Leu Lys Thr Ile Met Arg Glu Lys Tyr Ser Lys Cys Ser
        115                 120                 125

Ser

<210> SEQ ID NO 2
<211> LENGTH: 160
<212> TYPE: PRT
<213> ORGANISM: homo sapiens

<400> SEQUENCE: 2

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45
```

```
Lys Glu Ser Leu Leu Glu Asp Phe Lys Gly Tyr Leu Gly Cys Gln Ala
         50                  55                  60

Leu Ser Glu Met Ile Gln Phe Tyr Leu Glu Glu Val Met Pro Gln Ala
 65              70                  75                  80

Glu Asn Gln Asp Pro Asp Ile Lys Ala His Val Asn Ser Leu Gly Glu
                 85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
            115                 120                 125

Asn Lys Leu Gln Glu Lys Gly Ile Tyr Lys Ala Met Ser Glu Phe Asp
130                 135                 140

Ile Phe Ile Asn Tyr Ile Glu Ala Tyr Met Thr Met Lys Ile Arg Asn
145                 150                 155                 160

<210> SEQ ID NO 3
<211> LENGTH: 9
<212> TYPE: PRT
<213> ORGANISM: Artificial sequence
<220> FEATURE:
<223> OTHER INFORMATION: polypeptide linker

<400> SEQUENCE: 3

Gly Ser Gly Gly Gly Gly Ser Gly Thr
1               5

<210> SEQ ID NO 4
<211> LENGTH: 298
<212> TYPE: PRT
<213> ORGANISM: Artificial sequence
<220> FEATURE:
<223> OTHER INFORMATION: IL4-IL10 fusion protein

<400> SEQUENCE: 4

His Lys Cys Asp Ile Thr Leu Gln Glu Ile Ile Lys Thr Leu Asn Ser
1               5                   10                  15

Leu Thr Glu Gln Lys Thr Leu Cys Thr Glu Leu Thr Val Thr Asp Ile
            20                  25                  30

Phe Ala Ala Ser Lys Asn Thr Thr Glu Lys Glu Thr Phe Cys Arg Ala
        35                  40                  45

Ala Thr Val Leu Arg Gln Phe Tyr Ser His His Glu Lys Asp Thr Arg
    50                  55                  60

Cys Leu Gly Ala Thr Ala Gln Gln Phe His Arg His Lys Gln Leu Ile
65                  70                  75                  80

Arg Phe Leu Lys Arg Leu Asp Arg Asn Leu Trp Gly Leu Ala Gly Leu
                85                  90                  95

Asn Ser Cys Pro Val Lys Glu Ala Asn Gln Ser Thr Leu Glu Asn Phe
            100                 105                 110

Leu Glu Arg Leu Lys Thr Ile Met Arg Glu Lys Tyr Ser Lys Cys Ser
            115                 120                 125

Ser Gly Ser Gly Gly Gly Gly Ser Gly Thr Ser Pro Gly Gln Gly Thr
130                 135                 140

Gln Ser Glu Asn Ser Cys Thr His Phe Pro Gly Asn Leu Pro Asn Met
145                 150                 155                 160

Leu Arg Asp Leu Arg Asp Ala Phe Ser Arg Val Lys Thr Phe Phe Gln
                165                 170                 175

Met Lys Asp Gln Leu Asp Asn Leu Leu Leu Lys Glu Ser Leu Leu Glu
```

-continued

```
                    180                 185                 190
Asp Phe Lys Gly Tyr Leu Gly Cys Gln Ala Leu Ser Glu Met Ile Gln
            195                 200                 205

Phe Tyr Leu Glu Glu Val Met Pro Gln Ala Glu Asn Gln Asp Pro Asp
        210                 215                 220

Ile Lys Ala His Val Asn Ser Leu Gly Glu Asn Leu Lys Thr Leu Arg
225                 230                 235                 240

Leu Arg Leu Arg Arg Cys His Arg Phe Leu Pro Cys Glu Asn Lys Ser
                245                 250                 255

Lys Ala Val Glu Gln Val Lys Asn Ala Phe Asn Lys Leu Gln Glu Lys
                260                 265                 270

Gly Ile Tyr Lys Ala Met Ser Glu Phe Asp Ile Phe Ile Asn Tyr Ile
            275                 280                 285

Glu Ala Tyr Met Thr Met Lys Ile Arg Asn
        290                 295
```